(12) United States Patent
Kimura

(10) Patent No.: US 10,940,010 B2
(45) Date of Patent: Mar. 9, 2021

(54) ARTIFICIAL JOINT

(71) Applicant: NexMed International Co., Ltd., Chiba (JP)

(72) Inventor: Masahiro Kimura, Kanagawa (JP)

(73) Assignee: Nexmed International Co., Ltd., Chiba (JP)

( * ) Notice: Subject to any disclaimer, the term of this patent is extended or adjusted under 35 U.S.C. 154(b) by 47 days.

(21) Appl. No.: 16/331,686

(22) PCT Filed: Sep. 11, 2017

(86) PCT No.: PCT/JP2017/032719
§ 371 (c)(1),
(2) Date: Mar. 8, 2019

(87) PCT Pub. No.: WO2018/047967
PCT Pub. Date: Mar. 15, 2018

(65) Prior Publication Data
US 2019/0240031 A1 Aug. 8, 2019

(30) Foreign Application Priority Data
Sep. 10, 2016 (JP) .............................. JP2016-177180

(51) Int. Cl.
*A61F 2/34* (2006.01)
*A61F 2/32* (2006.01)
(Continued)

(52) U.S. Cl.
CPC ............ *A61F 2/34* (2013.01); *A61F 2/30734* (2013.01); *A61F 2/32* (2013.01); *A61F 2/3609* (2013.01);
(Continued)

(58) Field of Classification Search
CPC .. A61F 2/0734; A61F 2/32; A61F 2/34; A61F 2/36; A61F 2/38;
(Continued)

(56) References Cited

U.S. PATENT DOCUMENTS 4,642,123 A * 2/1987 Noiles ....................... A61F 2/32
623/22.2
2001/0032021 A1 10/2001 McKinnon
(Continued)

FOREIGN PATENT DOCUMENTS

JP 2003-526455 A 9/2003
JP 2005-021696 A 1/2005
(Continued)

OTHER PUBLICATIONS

Search Report in International Application No. PCT/JP2017/032719 dated Oct. 24, 2017, 4 pages.
(Continued)

*Primary Examiner* — Suba Ganesan
*Assistant Examiner* — Aren Patel
(74) *Attorney, Agent, or Firm* — Marshall, Gerstein & Borun LLP

(57) ABSTRACT

The artificial joint of the present invention is provided with a cup having a first housing part that opens on one first-direction side, an insert that is housed in the first housing part and has a second housing part that opens on one first-direction side, a movable member having a spherical head part rotatably housed in the second housing part and a neck part extending from the head part, and a connecting part that connects the insert to the cup pivotably around a pivotal axis extending in a second direction; the neck part contacting an edge part of the insert by pivoting around the pivotal axis; the insert pivoting around the pivotal axis; and part of the opposite side of the side pushed in by the neck
(Continued)

part across the pivotal axis protruding from the cup to one first-direction side.

15 Claims, 32 Drawing Sheets

(51) Int. Cl.
 *A61F 2/30* (2006.01)
 *A61F 2/36* (2006.01)
(52) U.S. Cl.
 CPC .............. *A61F 2002/30224* (2013.01); *A61F 2002/30242* (2013.01); *A61F 2002/30426* (2013.01); *A61F 2002/3208* (2013.01); *A61F 2002/3233* (2013.01); *A61F 2002/3625* (2013.01)
(58) Field of Classification Search
 CPC .. A61F 2002/30224; A61F 2002/30242; A61F 2002/3208; A61F 2002/3233; A61F 2002/3625
 USPC ...................................................... 623/22.15
 See application file for complete search history.

(56) References Cited

U.S. PATENT DOCUMENTS

| | | |
|---|---|---|
| 2005/0004678 A1 | 1/2005 | Richards |
| 2006/0241780 A1 | 10/2006 | McKinnon |
| 2007/0106389 A1 | 5/2007 | Croxton et al. |
| 2007/0191961 A1 | 8/2007 | Aux Epaules et al. |
| 2012/0209397 A1 | 8/2012 | Richardson |
| 2012/0209398 A1 | 8/2012 | Richardson et al. |
| 2013/0345822 A1 | 12/2013 | Grostefon et al. |

FOREIGN PATENT DOCUMENTS

| | | |
|---|---|---|
| JP | 2007-215989 A | 8/2007 |
| JP | 2012-183303 A | 9/2012 |
| JP | 2012-183304 A | 9/2012 |
| JP | 2014/004360 A | 1/2014 |

OTHER PUBLICATIONS

International Preliminary Report on Patentability in International Application No. PCT/JP2017/032719 dated Mar. 21, 2019, 11 pages.

* cited by examiner (A)

(B)

(A)

(B)

(C)

(A)

(B)

(C)

(A)

(B)

(C)

(A)

(B)

(C)

ARTIFICIAL JOINT

CROSS REFERENCE TO RELATED APPLICATIONS

This application is based upon and claims the benefit of priority of the prior Japanese Patent Application No. 2016-177180, filed on Sep. 10, 2016, and International Patent Application No. PCT/JP2017/032719, filed on Sep. 11, 2017, the entire contents of which are incorporated herein by reference.

TECHNICAL FIELD

The present invention relates to an artificial joint.

BACKGROUND ART

Conventionally, artificial joints for suppressing dislocation have been proposed. For example, as an artificial joint, JP 2003-526455 A describes an artificial hip joint in which a high wall is provided in a part of a cup margin and the head of a femoral implant is less likely to deviate towards a side provided with a high wall. Hereinafter, a cup having such a high wall is referred to as a "fixed high wall type cup". For example, as an artificial joint, JP 2005-021696 A describes an artificial hip joint in which a cup encases a bone head portion by making the inner diameter of the opening of the deepened cup narrower than the diameter of the bone head portion and hence deviation of the bone head portion from the cup is suppressed. This cup is a kind of cup so-called "restraint type cup".

SUMMARY OF INVENTION

Technical Problem

For example, the dislocation suppression effect due to the high wall of the fixed high wall type cup as shown in Patent Literature 1 can be increased with an increase in the height of the high wall. On the other hand, however, there is a problem that the larger the high wall is, the more the neck portion of the femoral implant is likely to come into contact with the high wall and a range of motion of a joint decreases. There is another problem that with respect to the side opposite to the side provided with the high wall, the bone head portion is liable to deviate from the cup, and it is not possible to obtain a sufficient dislocation suppression effect. Further, in an artificial hip joint having a restraint type cup as disclosed in Patent Literature 2, for example, the neck portion and the cup margin are easily in contact with each other, and the range of motion of the joint decreases. There is a problem that decrease of the range of motion of the joint results in a greatly impairment in the degree of freedom of motion of a patient wearing the artificial joint.

As described above, in a conventional artificial joint, ensuring the range of motion of the joint and obtaining a sufficient dislocation suppression effect conflict with each other, and it is hence difficult to obtain these two at the same time.

In view of the above circumstances, it is an object of the present invention to provide an artificial joint capable of sufficiently suppressing dislocation while ensuring the range of motion of the joint.

Solution to Problem

One aspect of an artificial joint of the present invention includes: a cup having a first housing portion opening to one side in a first direction; an insert having a second housing portion opening to one side in the first direction and being housed in the first housing portion; a movable member having a spherical bone head portion rotatably housed in the second housing portion and a neck portion extending from the bone head portion; and a coupling portion coupling the insert to the cup so as to be pivotable about a pivotal axis extending in a second direction orthogonal to the first direction and regulates movement to one side in the first direction of the insert relative to the cup, wherein the neck portion pivots about the pivotal axis and comes into contact with a periphery portion of the insert, thereby pushing a part of the insert into the first housing portion, and the insert pivots about the pivotal axis by the part of the insert being pushed by the neck portion and a portion on a side opposite across the pivotal axis to a side pushed by the neck portion protrudes more to one side in the first direction than the cup.

The coupling portion may be configured to have a recess portion provided in one of the cup and the insert, and a projection portion provided in the other of the cup and the insert and fitted in the recess portion.

The insert may be configured to have an insert body portion, and a protrusion portion protruding from the insert body portion towards one side in the first direction, and the protrusion portion may be provided on each of both sides across the pivotal axis.

Advantageous Effects of Invention

According to one aspect of the present invention, there is provided an artificial joint capable of sufficiently suppressing dislocation while ensuring the range of motion of the joint.

DETAILED DESCRIPTION OF THE INVENTION

Hereinafter, as an artificial joint according to an embodiment of the present invention, an example of an artificial hip joint will be described with reference to the drawings. The scope of the present invention is not limited to the following embodiments, and can be arbitrarily changed within the technical idea of the present invention. Also, in the following drawings, the scale, the number, and the like in each structure may be different from the scale, the number, and the like in the actual structure in order to make each configuration easy to understand.

In the XYZ coordinate system appropriately shown in each drawing, the Z axis direction is defined as a "first direction Z", the X axis direction is defined as a "second direction X" orthogonal to the first direction Z, and the Y axis direction is defined as a "third direction Y" orthogonal to both of the first direction Z and the second direction X. Further, the negative side (−Z side) of the Z axis direction is referred to as a "one side in the first direction" and the positive side (+Z side) of the Z axis direction is referred to as an "other side in the first direction".

In the explanation of the relative positional relationship between portions in the following embodiments, unless otherwise noted, an artificial hip joint assumes a reference posture in which an opening cross-section of a second housing portion of an insert is perpendicular to the first direction Z.

In addition, in the following description, the names of directions of the body such as anteroposterior, craniocaudal, and external-internal, and the names of the joint motion such as flexion, extension, lateral rotation, and medial rotation in accordance with the usage of terms used in anatomy, orthopedic surgery, and the like as appropriate.

First Embodiment

Figure 1:
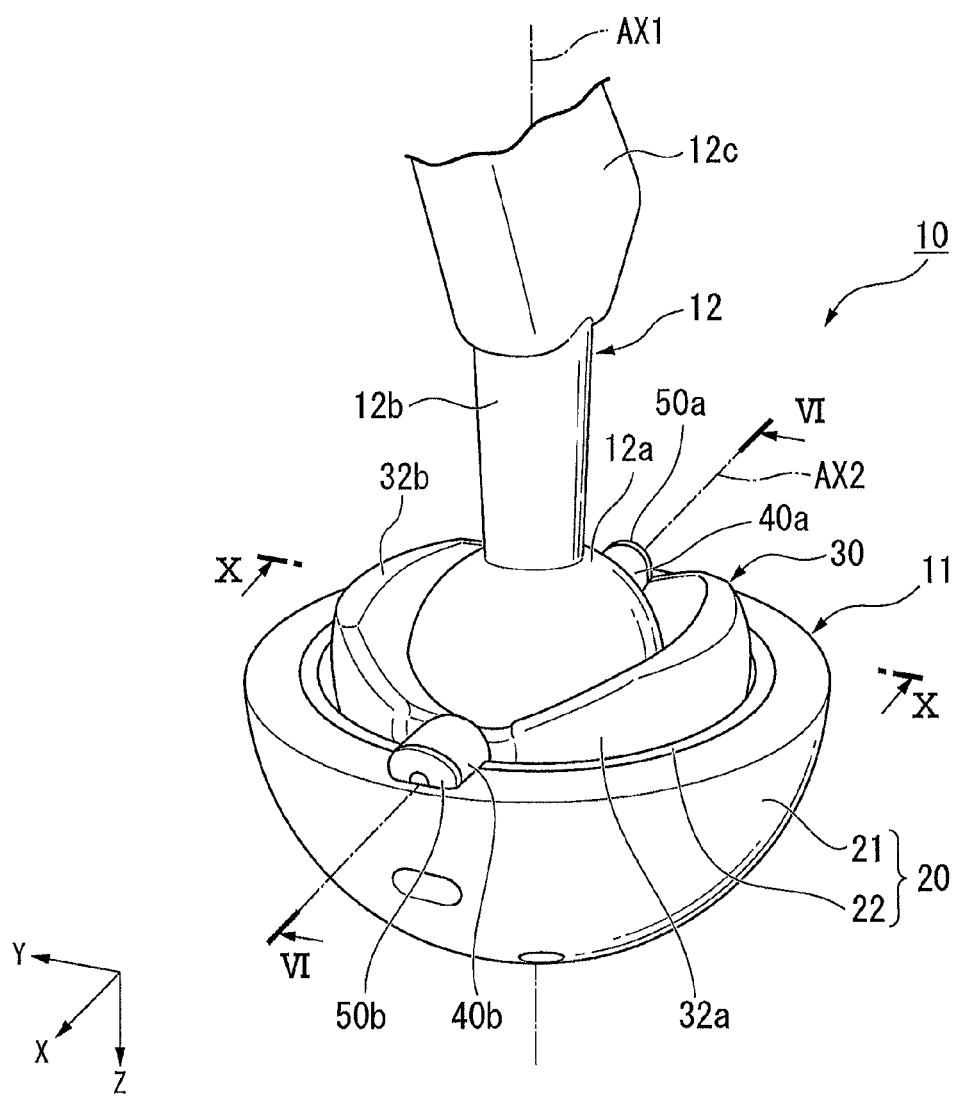
FIG. 1 is a perspective view showing an artificial hip joint of a first embodiment.
Figure 2:
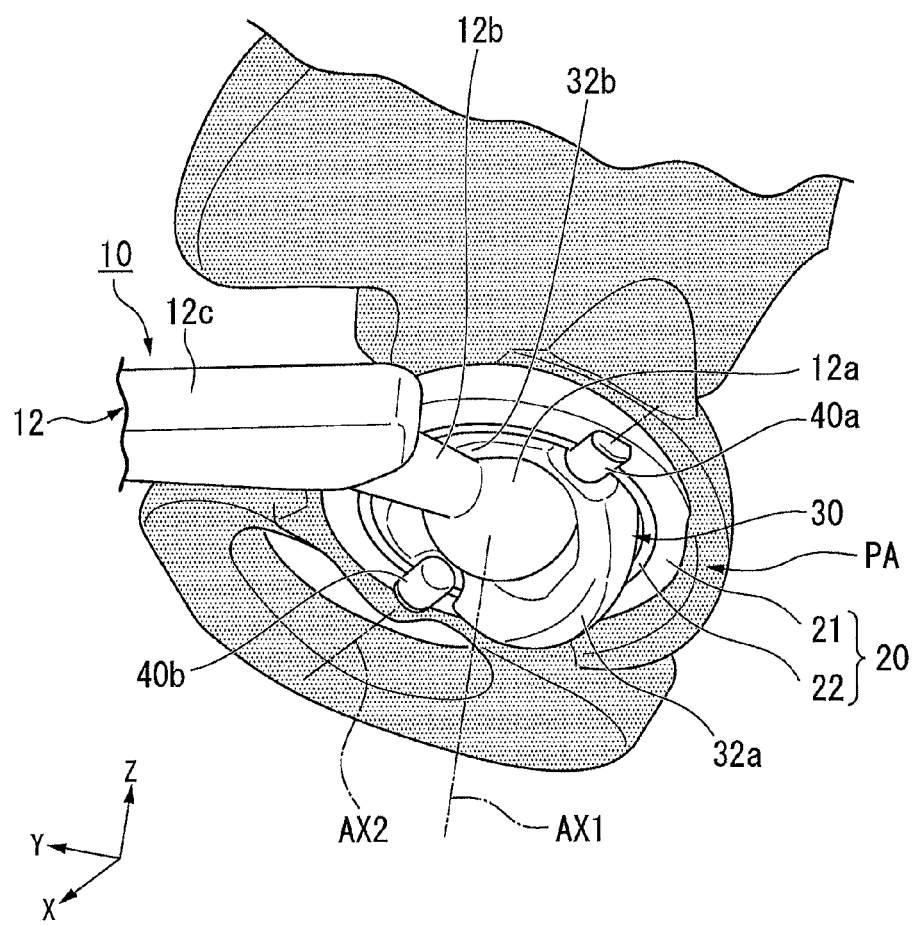
FIG. 2 is a perspective view showing a state in which the artificial hip joint of the first embodiment is attached to the pelvic acetabulum.
Figure 3:
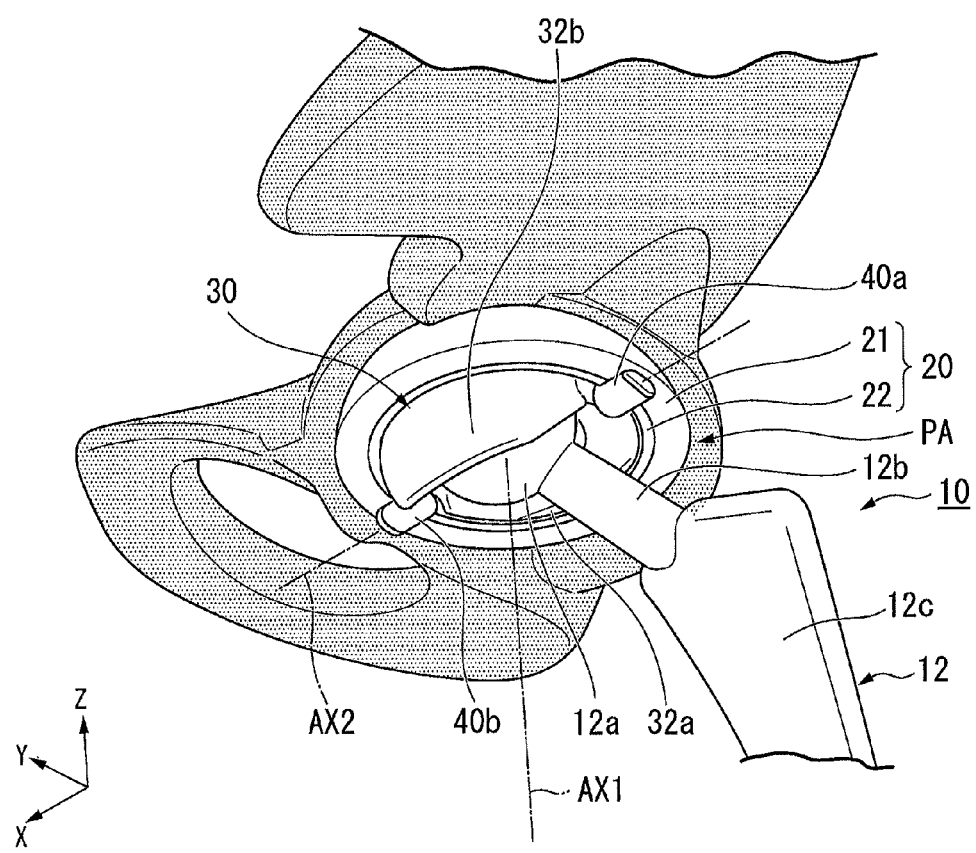
FIG. 3 is a perspective view showing a state in which the artificial hip joint of the first embodiment is attached to the pelvic acetabulum.
Figure 4:
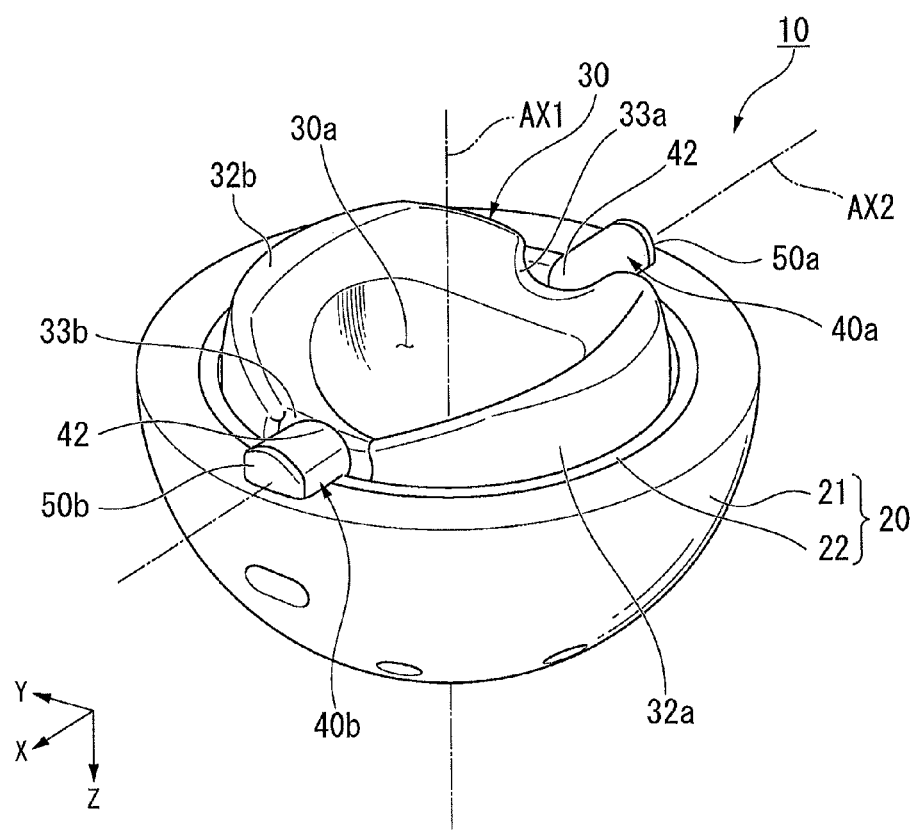
FIG. 4 is a perspective view showing a part of the artificial hip joint of the first embodiment.
Figure 5:
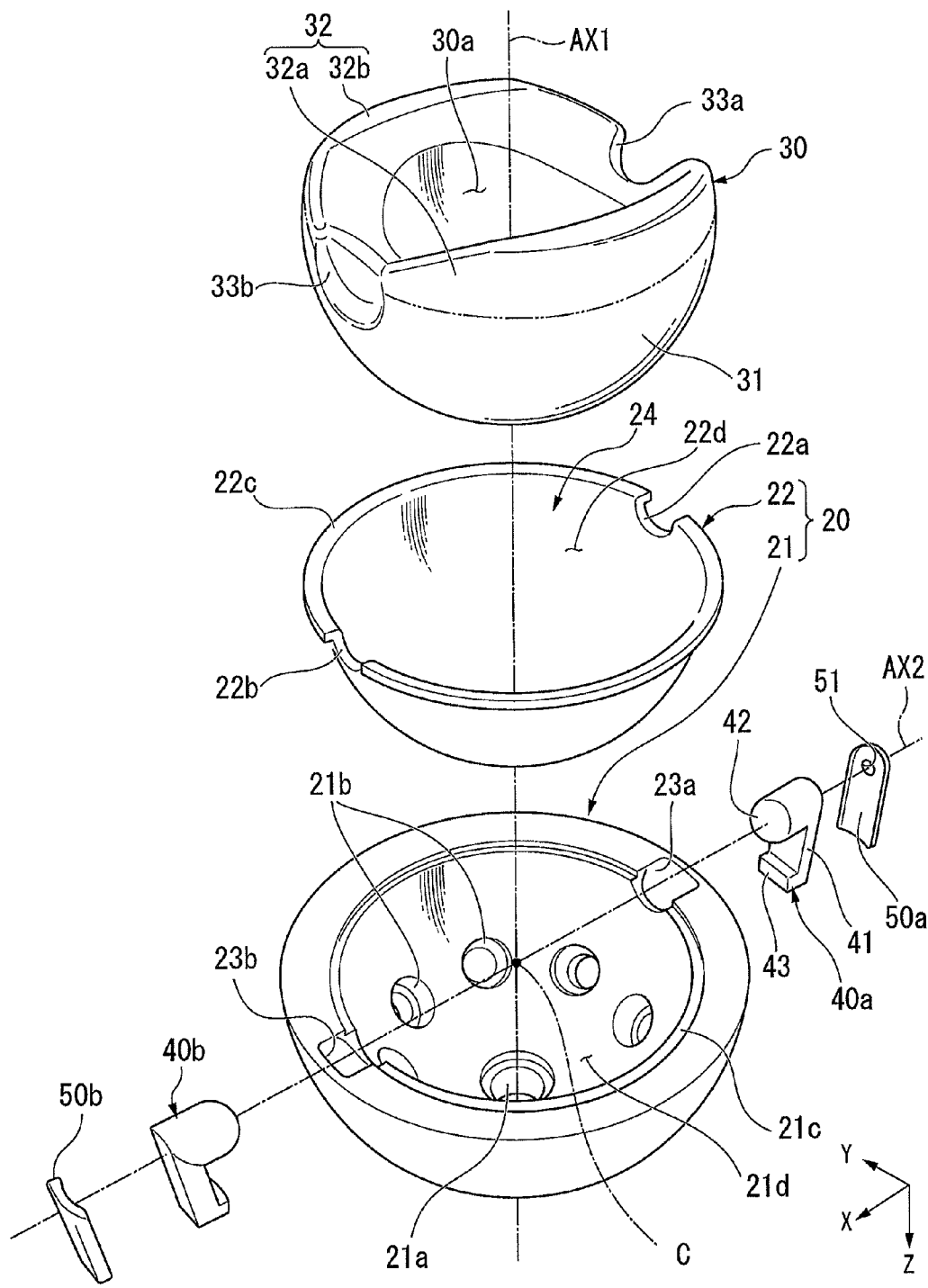
FIG. 5 is an exploded perspective view showing a part of the artificial hip joint of the first embodiment.
Figure 6:
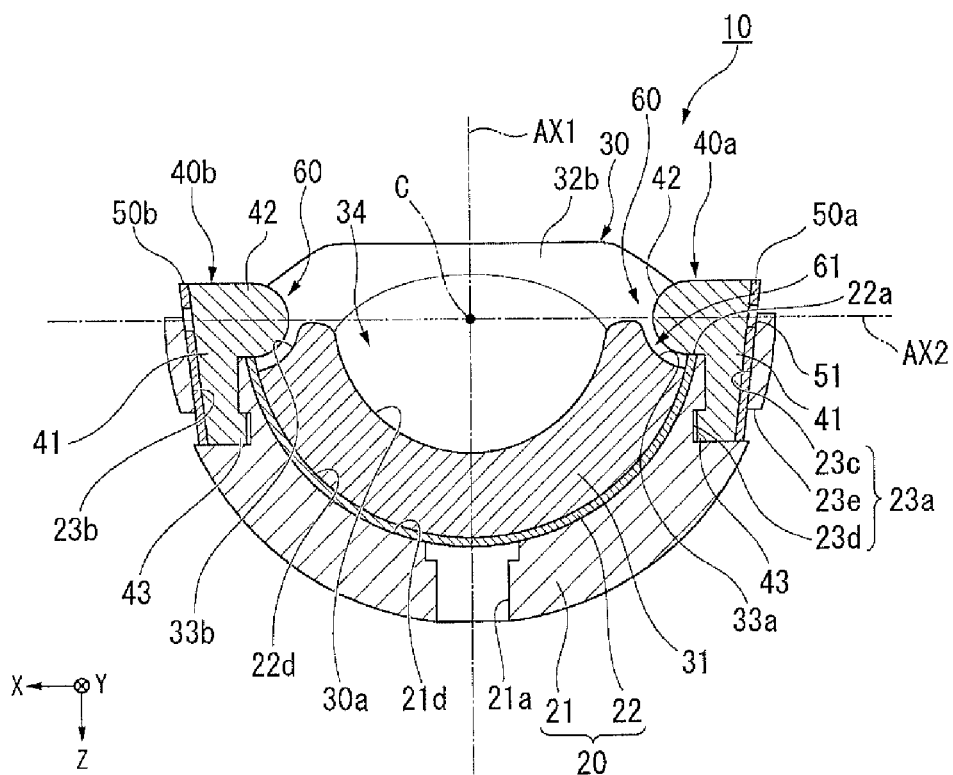
FIG. 6 is a view showing a part of the artificial hip joint of the first embodiment and is a sectional view taken along a line V-V in FIG. 1.

FIG. 1 is a perspective view showing an artificial hip joint (artificial joint) 10 of the present embodiment. FIG. 2 and FIG. 3 are perspective views showing a state in which the artificial hip joint 10 of the present embodiment is attached to a pelvic acetabulum PA. FIG. 4 is a perspective view showing a part of the artificial hip joint 10 of the present embodiment. FIG. 5 is an exploded perspective view showing a part of the artificial hip joint 10 of the present embodiment. FIG. 6 is a view showing a part of the artificial hip joint 10 of the present embodiment, and is a sectional view taken along the line VI-VI in FIG. 1. FIG. 1 shows a case where the artificial hip joint 10 of the present embodiment is in the reference posture. FIG. 2 shows a case of the hip joint flexion and medial rotation. FIG. 3 shows a case of the hip joint extension and lateral rotation. In FIG. 2 and FIG. 3, the left side of the figure is the anterior side and the right side of the figure is the posterior side.

As shown in FIG. 1 to FIG. 3, the artificial hip joint 10 of the present embodiment includes a cup 20, pivot support shafts 40a and 40b, support shaft fasteners 50a and 50b, an insert 30, and a femoral implant (movable member) 12.

The cup 20 is fixed to the pelvic acetabulum PA as shown in FIG. 2 and FIG. 3. As shown in FIG. 4 and FIG. 5, the cup 20 has a hemispherical, shell-shaped protruding to the other side (+Z side) in the first direction. The inside of the cup 20 opens to one side (−Z side) in the first direction. The center of the hollow hemispherical cup 20 is a center point C that is an intersection of a central axis AX1 extending in the first direction Z and a pivotal axis AX2 extending in the second direction X.

In the following description, the radial direction about the center point C is simply referred to as "radial", "radially", or "radial direction", and the circumferential direction about the central axis AX1 is simply referred to as "circumferential", "circumferentially", or "circumferential direction". With respect to a certain object, a side close to the central axis AX1 in the second direction X is referred to as a "second direction inner side" and a side far from the central axis AX1 in the second direction X is referred to as a "second direction outer side". With respect to a certain object, a side close to the central axis AX1 in the third direction Y is referred to as a "third direction inner side".

In the present embodiment, the cup 20 has a cup body portion 21 and a sliding surface component 22. As shown in FIG. 5, the cup body portion 21 has a hemispherical, shell-shaped protruding to the other side (+Z side) in the first direction. The inside of the cup body portion 21 opens on one side (−Z side) in the first direction. An opening periphery portion of the cup body portion 21 on one side in the first direction of the cup body portion 21 is provided with a bump portion 21c recessed towards the other side in the first direction from the radially outer side to the radially inner side. The bump portion 21c is provided over substantially the entire circumference along the circumferential direction.

Screw insertion holes 21a and 21b radially penetrating a wall portion of the cup body portion 21 from an inner side surface 21d of the cup body portion 21 to an outer side surface are formed on the inner side surface 21d of the cup body portion 21. The screw insertion bore 21a penetrates the cup body portion 21 in the first direction Z. The plurality of screw insertion bores 21b are provided around the screw insertion bore 21a along the circumferential direction. Into the screw insertion bores 21a and 21b, screws to be screwed into the pelvic acetabulum PA are passed. With the screws passing through the screw insertion bores 21a and 21b, the cup body portion 21 is fixed to the pelvic acetabulum PA and the cup 20 is fixed to the pelvic acetabulum PA.

Pivot support shaft insertion holes 23a and 23b that are recessed towards the other side (+Z side) in the first direction are formed at the end portion of one side (−Z side) in the first direction of the cup body portion 21. The pivot support shaft insertion hole 23a and the pivot support shaft insertion hole 23b are provided across the central axis AX1 (center point C) in the second direction X. Since the pivot support shaft insertion hole 23a and the pivot support shaft insertion hole 23b have the same configuration except that they are arranged symmetrically in the second direction X across the central axis AX1, only the pivot support shaft insertion hole 23a may be described as a representative in the following description.

As shown in FIG. 6, the pivot support shaft insertion hole 23a has a stretch hole portion 23c extending in the first direction Z, an engagement portion 23d recessed towards the second direction inner side from the end portion of the other side (+Z side) in the first direction of the stretch hole portion 23c, and a penetration portion 23e penetrating from the outer side surface of the cup body portion 21 to the end portion of the other side in the first direction of the stretch hole portion 23c. The end portion on one side (−Z side) in the first direction of the stretch hole portion 23c opens to one side in the first direction and in the second direction inner side.

As shown in FIG. 5, the sliding surface component 22 has a hemispherical, shell-shaped protruding to the other side (+Z side) in the first direction. The radial thickness of the sliding surface component 22 is smaller than the radial thickness of the cup body portion 21. As shown in FIG. 4 and FIG. 6, the sliding surface component 22 is inserted into the inside of the cup body portion 21. The sliding surface component 22 is fixed with the cup body portion 21 by fitting the outer side surface of the sliding surface component 22 into the inside of the cup body portion 21 along the inner side surface 21d of the cup body portion 21. As shown in FIG. 5, a flange portion 22c protruding radially outward is provided at the end portion on one side (−Z side) in the first direction of the sliding surface component 22. The flange portion 22c is fitted to the bump portion 21c of the cup body portion 21.

Notch portions 22a and 22b recessed towards the other side (+Z side) in the first direction are formed at the end portion on one side (−Z side) in the first direction of the sliding surface component 22. The notch portion 22a and the notch portion 22b are provided across the central axis AX1 (center point C) in the second direction X. The notch portions 22a and 22b radially penetrate the wall portion of the sliding surface component 22 from the outer side surface to the inner side surface of the sliding surface component 22. In the second direction inner side of the pivot support shaft insertion hole 23a, the notch portion 22a faces the end portion on one side in the first direction of the pivot support shaft insertion hole 23a in the second direction X. In the second direction inner side of the pivot support shaft insertion hole 23b, the notch portion 22b faces the end portion on one side in the first direction of the pivot support shaft insertion hole 23b in the second direction X.

The cup 20 has a first housing portion 24 that opens to one side (−Z side) in the first direction. In the present embodiment, the first housing portion 24 is the inside of the sliding surface component 22. The inner side surface of the first housing portion 24, i.e., an inner side surface 22d of the sliding surface component 22 is a hemispherical surface recessed towards the other side (+Z side) in the first direction, and is a sliding surface on which the insert 30 slides.

The pivot support shafts 40a and 40b are inserted into the pivot support shaft insertion holes 23a and 23b, respectively, and are mounted on the cup 20. Since the pivot support shaft 40a and the pivot support shaft 40b have the same configuration except that they are arranged symmetrically in the second direction X across the central axis AX1, only the pivot support shaft 40a may be described as a representative in the following description.

The pivot support shaft 40a has an insertion portion 41 extending in the first direction Z, a shaft body portion (projection portion) 42 extending to the second direction inner side from the end portion on one side (−Z side) in the first direction of the insertion portion 41, and an engagement protrusion 43 protruding to the second direction inner side from the end portion of the other side (+Z side) in the first direction of the insertion portion 41. As shown in FIG. 6, the insertion portion 41 is inserted into the stretch hole portion 23c of the pivot support shaft insertion hole 23a. The end portion on one side in the first direction of the insertion portion 41 protrudes to one side in the first direction than the pivot support shaft insertion hole 23a. The surface on the second direction inner side of the insertion portion 41 is in contact with the surface on the second direction inner side of the stretch hole portion 23c.

A shaft body portion 42 is cylindrical about the pivotal axis AX2. The shaft body portion 42 protrudes radially inward than the inner side surface 22d of the sliding surface component 22 via the notch portion 22a of the sliding surface component 22. A top end portion of the shaft body portion 42 is hemispherical protruding to the second direction inner side (radially inward). The engagement protrusion 43 is inserted into and engaged with the engagement portion 23d of the pivot support shaft insertion hole 23a.

The support shaft fasteners 50a and 50b are members for fixing the pivot support shafts 40a and 40b, respectively. Since the support shaft fastener 50a and the support shaft fastener 50b have the same configuration except that they are arranged symmetrically in the second direction X across the central axis AX1, only the support shaft fastener 50a may be described as a representative in the following description.

As shown in FIG. 5, the support shaft fastener 50a is in a plate shape extending in the first direction Z and having a plate surface oriented in the second direction X. In the support shaft fastener 50a, a through hole 51 penetrating the support shaft fastener 50a in the second direction X is formed. The pivotal axis AX2 passes through the through hole 51. As shown in FIG. 6, the support shaft fastener 50a is inserted into the pivot support shaft insertion hole 23a. The end portion on one side (−Z side) in the first direction of the support shaft fastener 50a protrudes to one side in the first direction than the pivot support shaft insertion hole 23a.

The end portion on one side in the first direction of the support shaft fastener 50a is at the same position as the end portion on one side in the first direction of the pivot support shaft 40a, for example, in the first direction Z.

The support shaft fastener 50a is arranged second direction outer side of the pivot support shaft 40a. The surface on the second direction inner side of the support shaft fastener 50a is in contact with the surface of the second direction outer side of the pivot support shaft 40a. The surface on the second direction outer side of the support shaft fastener 50a is in contact with the surface of the second direction outer side of the stretch hole portion 23c in the pivot support shaft insertion hole 23a. The end portion of the other side (+Z side) in the first direction of the support shaft fastener 50a blocks the end portion of the second direction inner side of the penetration portion 23e in the pivot support shaft insertion hole 23a.

As shown in FIG. 5, the insert 30 has a substantially hemispherical, shell-shaped protruding to the other side (+Z side) in the first direction and opening on one side (−Z side) in the first direction. The insert 30 is housed in the first housing portion 24 of the cup 20. The insert 30 has a hemispherical shell-like insert body portion 31 and a protrusion portion 32 protruding from the insert body portion 31 towards one side in the first direction. Bearing recesses (recess portions) 33a and 33b recessed towards the second direction inner side are formed at both end portions of the second direction X in the insert body portion 31. The bearing recesses 33a and 33b open on one side in the first direction.

As shown in FIG. 6, the shaft body portions 42 of the pivot support shafts 40a and 40b are fitted to the bearing recesses 33a and 33b. Due to this, in the present embodiment, a coupling portion 60 having the bearing recesses 33a and 33b as the recess portions and the shaft body portion 42 as the projection portion is constituted. The coupling portion 60 couples the insert 30 to the cup 20 so as to be pivotable about the pivotal axis AX2. The shaft body portion 42 fitted to the bearing recesses 33a and 33b is arranged facing one side (−Z side) in the first direction of the surface of the other side (+Z side) in the first direction of the inner side surfaces of the bearing recesses 33a and 33b. Therefore, when the insert 30 moves to one side in the first direction with respect to the cup 20, the inner side surfaces of the bearing recesses 33a and 33b come into contact with the shaft body portion 42. In this manner, the coupling portion 60 regulates the insert 30 from moving towards one side in the first direction with respect to the cup 20 and suppresses the insert 30 from coming off from the cup 20.

In the present embodiment, the recess and projection fitting of the coupling portion 60 is, for example, a loose fitting to some extent, and a gap 61 is provided between the bearing recesses 33a and 33b and the shaft body portion 42. The dimension of the gap 61 is preferably 1 to 3 mm, and more preferably 1 to 1.5 mm. As a result, the insert 30 is movable in a direction (for example, the first direction −Z side) orthogonal to the pivotal axis AX2 to an extent that the insert 30 does not completely deviate from the cup 20.

As shown in FIG. 5, the protrusion portion 32 includes a protrusion portion 32a protruding from one side (−Y side) in the third direction Y of the end portion on one side (−Z side) in the first direction of the insert body portion 31 to one side in the first direction and a protrusion portion 32b protruding from the other side (+Y side) in the third direction Y of the end portion on one side in the first direction of the insert body portion 31 to one side in the first direction. The protrusion portion 32a and the protrusion portion 32b are positioned on both sides across the pivotal axis AX2 in the third direction Y. That is, in the present embodiment, the protrusion portion 32 is provided on each of the both sides across the central axis AX1 and the pivotal axis AX2. Since the protrusion portion 32a and the protrusion portion 32b have the same configuration except that they are arranged symmetrically in the second direction X across the central axis AX1, only the protrusion portion 32a may be described as a representative in the following description.

The protrusion portion 32a extends along the circumferential direction. The end face on one side (−Z side) in the first direction of the protrusion portion 32a is a flat surface. The protrusion height of the protrusion portion 32a decreases towards the circumferential end portion in the portions on both circumferential sides of the protrusion portion 32a. The radial dimension of the protrusion portion 32a decreases from the other side in the first direction towards one side (−Z side) in the first direction. The radially outer side surface of the protrusion portion 32a is smoothly connected to the radially outer side surface of the insert body portion 31.

Figure 7:
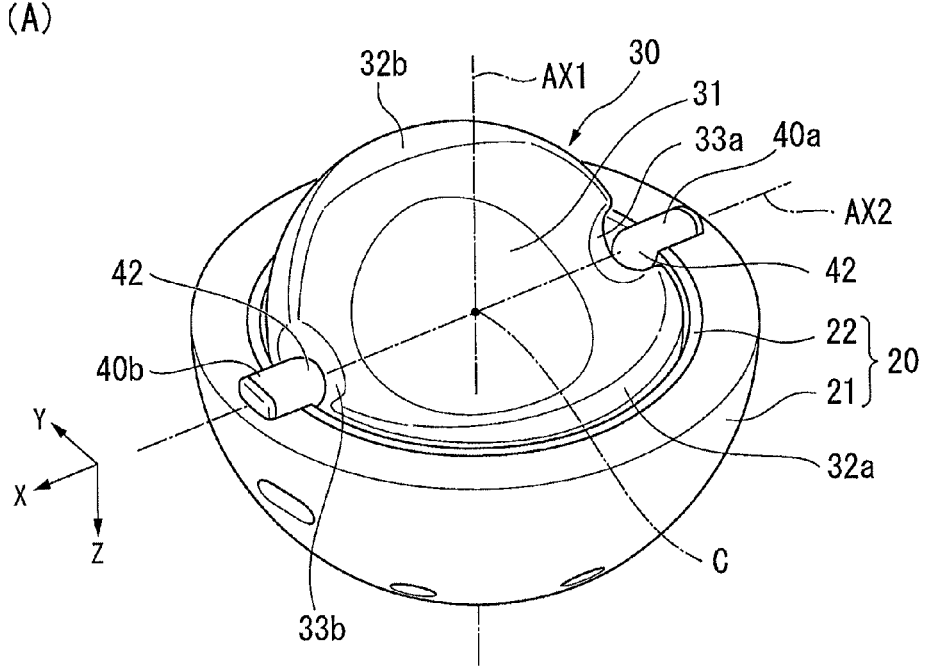
FIGS. 7A and 7B are views showing a state in which an insert of the first embodiment pivots from a reference posture with respect to a cup.
Figure 7:
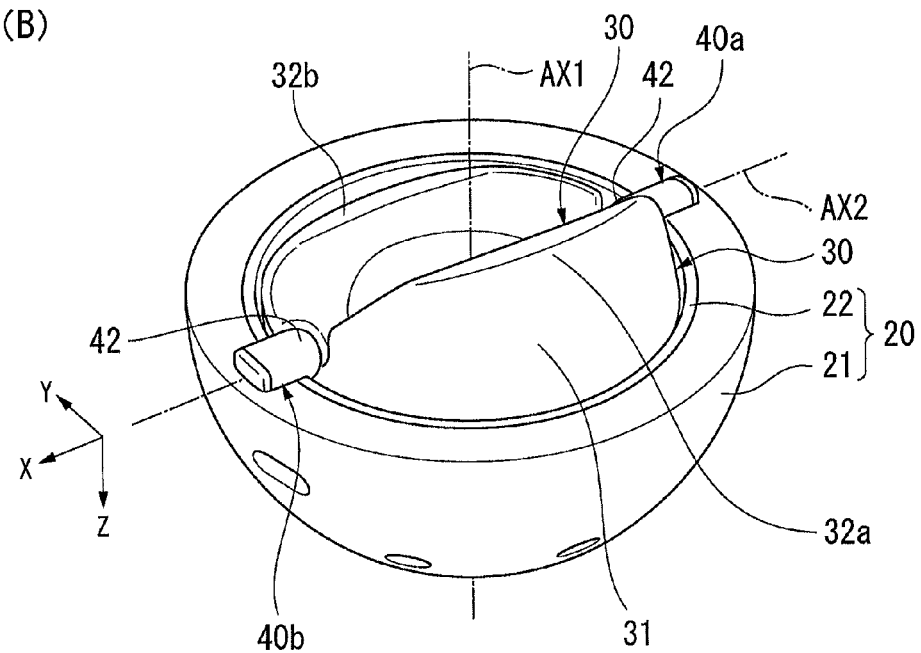

FIGS. 7A and 7B are views showing a state in which the insert 30 pivots from the reference posture with respect to the cup 20. As shown in FIG. 7(A), when the insert 30 pivots in one direction (clockwise direction as viewed from the +X side) about the pivotal axis AX2 with respect to the cup 20, the protrusion portion 32a enters inside the cup 20 and the protrusion portion 32b protrudes to one side (−Z side) in the first direction. On the other hand, as shown in FIG. 7 (B), when the insert 30 pivots in the other direction (counterclockwise direction as viewed from the +X side) about the pivotal axis AX2 with respect to the cup 20, the protrusion portion 32b enters inside the cup 20 and the protrusion portion 32b protrudes to one side in the first direction.

As shown in FIG. 6, the insert 30 has a second housing portion 34 that opens to one side (−Z side) in the first direction. In the present embodiment, the second housing portion 34 is the inside of the insert body portion 31. The opening portion of the second housing portion 34 has a size equal to or larger than the maximum cross-section of a bone head portion 12a described later. The inner side surface of the second housing portion 34, i.e., an inner side surface 30a of the insert body portion 31 is a hemispherical surface that is recessed towards the other side (+Z side) in the first direction and is a sliding surface on which the bone head portion 12a slides.

As shown in FIG. 1, a femoral implant 12 has the spherical bone head portion 12a, a neck portion 12b, and a stem portion 12c. The bone head portion 12a is rotatably housed in the second housing portion 34 of the insert 30. The neck portion 12b extends from the bone head portion 12a to one side (−Z side) in the first direction. The stem portion 12c is connected to the end portion of the neck portion 12b on the opposite side to the bone head portion 12a. The stem portion 12c is, for example, a portion to be embedded in the femur.

Figure 8:
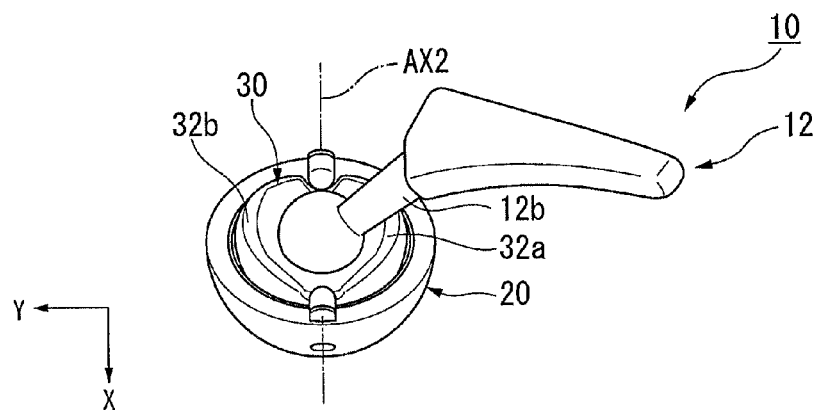
FIGS. 8A-8C are perspective views for explaining an operation of the artificial hip joint of the first embodiment.
Figure 8:
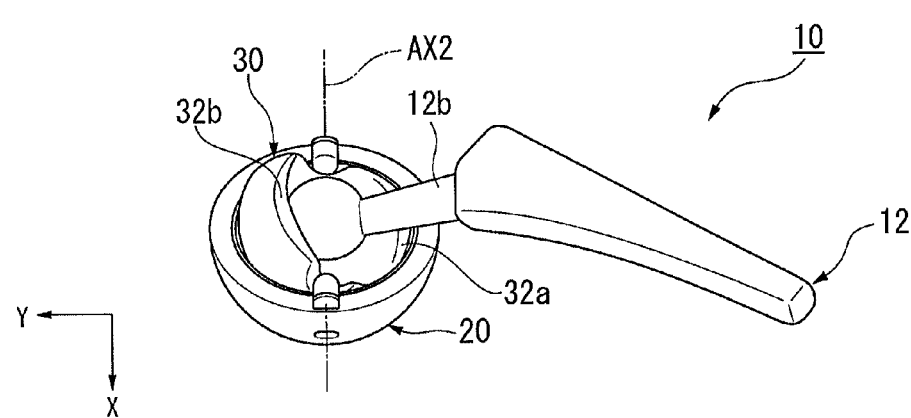
Figure 8:
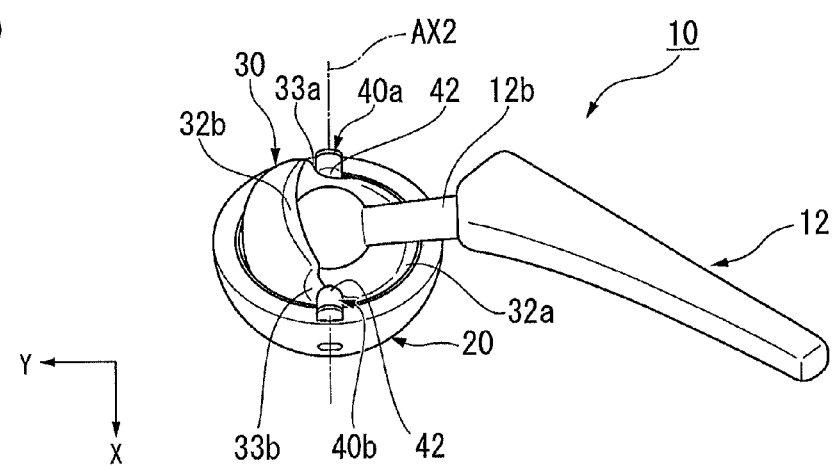
Figure 9:
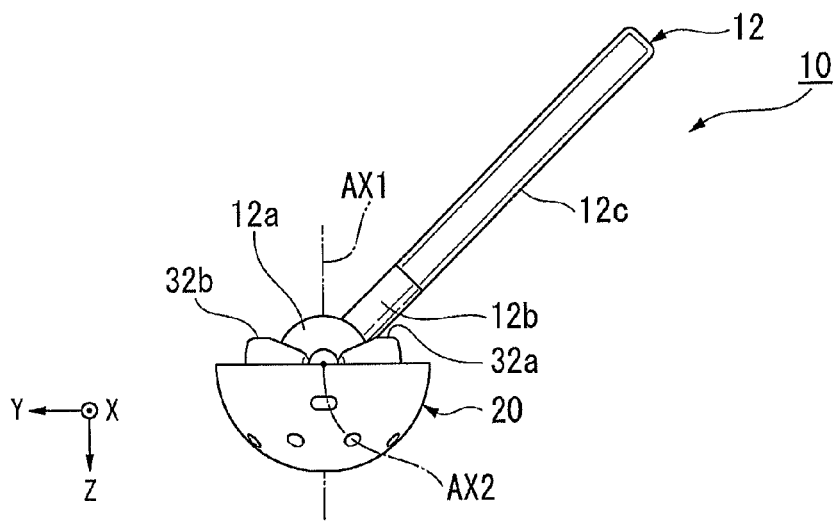
FIGS. 9A-9C are views for explaining the operation of the artificial hip joint of the first embodiment, as viewed along a second direction.
Figure 9:
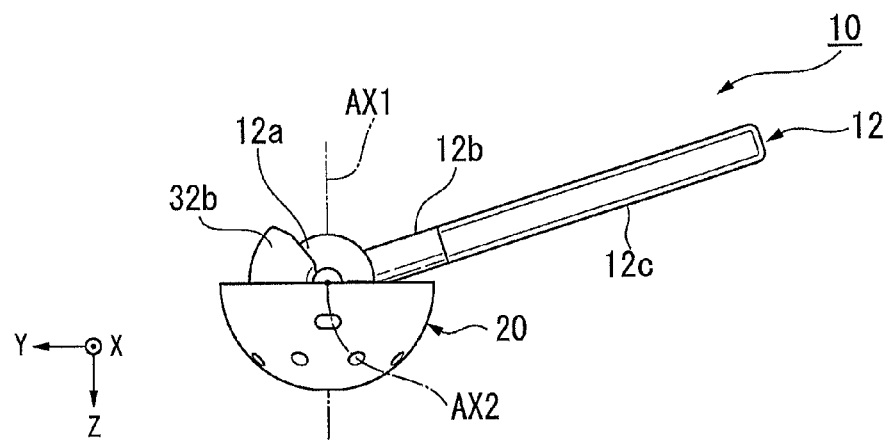
Figure 9:
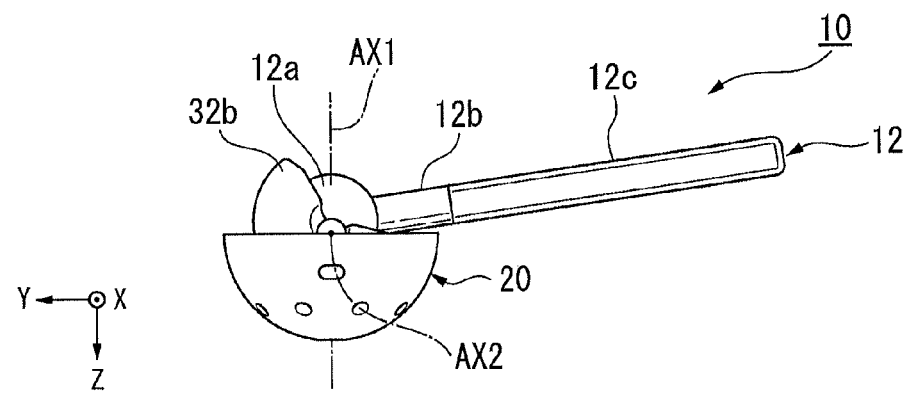
Figure 10:
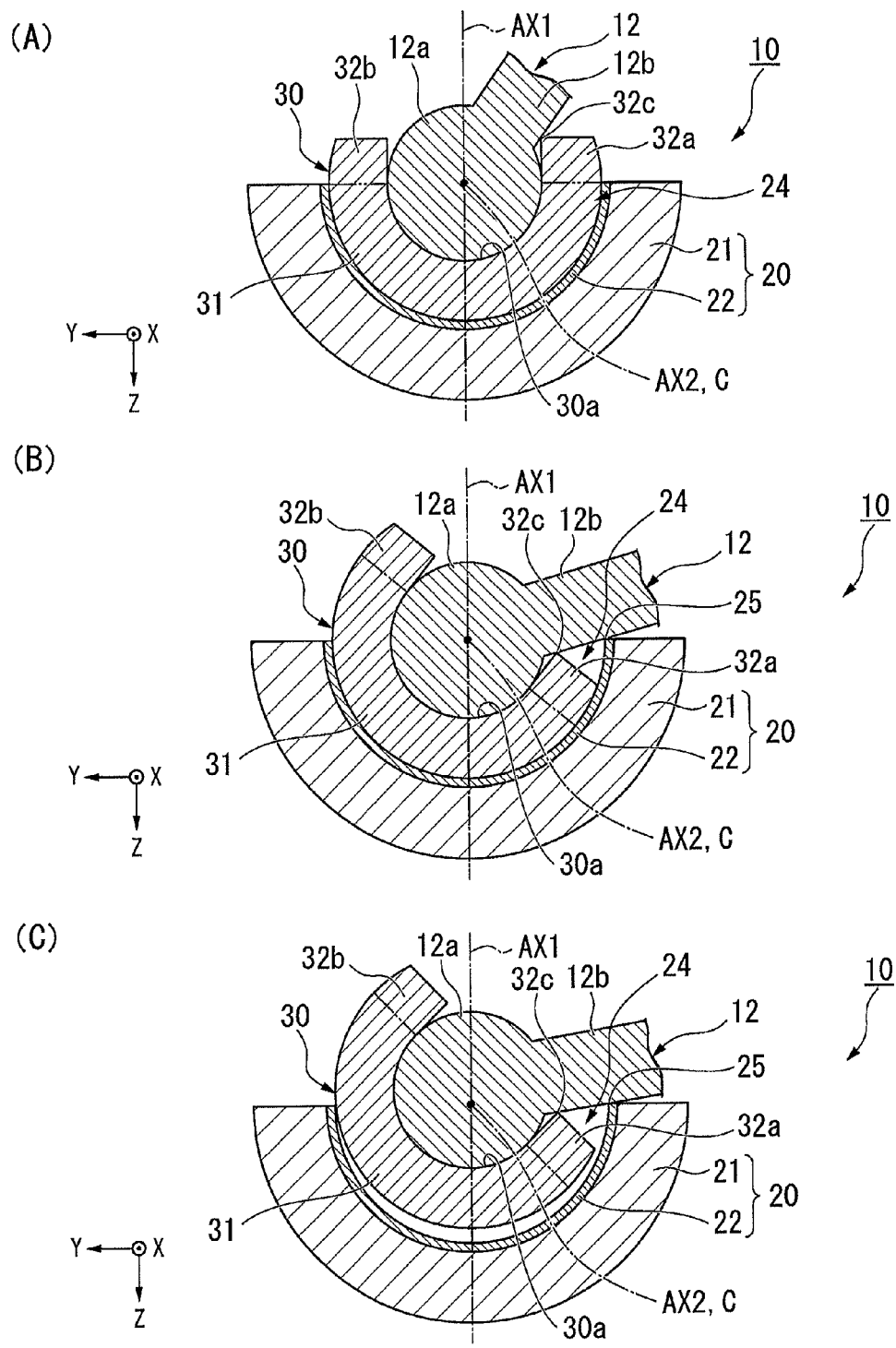
FIGS. 10A-10C are views for explaining the operation of the artificial hip joint of the first embodiment, schematically showing an X-X section in FIG. 1.

Next, the operation of the artificial hip joint 10 of the present embodiment will be described. FIGS. 8A-8C are perspective views for explaining the operation of the artificial hip joint 10. FIGS. 9A-9C are views for explaining the operation of the artificial hip joint 10, as viewed along the second direction X. FIGS. 10A-10C are views for explaining the operation of the artificial hip joint 10, schematically showing the X-X section in FIG. 1.

FIGS. 8A to 10C show a case where the femoral implant 12 pivots in one direction (clockwise direction as viewed from the +X side) about the pivotal axis AX2. The case where the femoral implant 12 pivots in one direction about the pivotal axis AX2 corresponds to, for example, a case where the patient wearing the artificial hip joint 10 has his hip joint extended and laterally rotated as shown in FIG. 3.

As shown in FIGS. 8A, 9A, and 10A, when the femoral implant 12 pivots, the neck portion 12b comes into contact with an edge portion 32c of the insert 30. As shown in FIG. 10A, in the present embodiment, the edge portion 32c of the insert 30 is an edge of the inner side in the third direction at the end portion on one side (−Z side) in the first direction of the protrusion portion 32a. When the femoral implant 12 further pivots in a state where the neck portion 12b is in contact with the edge portion 32c, as shown in FIG. 8B, FIG. 9B, and FIG. 10B, the edge portion 32c is pushed to the neck portion 12b, and the insert 30 pivots about the pivotal axis AX2. As a result, the protrusion portion 32a is pushed into the first housing portion 24. In this manner, by pivoting about the pivotal axis AX2, the neck portion 12b comes into contact with the edge portion 32c of the insert 30 and pushes a part of the insert 30 into the first housing portion 24.

When the protrusion portion 32a is pushed into the first housing portion 24 and the insert 30 pivots, the protrusion portion 32b on the opposite side across the pivotal axis AX2 protrudes more to one side (−Z side) in the first direction than the cup 20. That is, a part of the insert 30 is pushed into by the neck portion 12b, hence the insert 30 pivots about the pivotal axis AX2 and a portion on the opposite side across the pivotal axis AX2 to the side on which it is pushed into by the neck portion 12b protrudes more towards one side in the first direction than the cup 20.

In the state shown in FIGS. 8B, 9B, and 10B, the neck portion 12b is in contact with an edge portion 25 of the cup 20. In the present embodiment, the edge portion 25 is an edge portion of the sliding surface component 22. When the femoral implant 12 further pivots from this state, as shown in FIGS. 8C, 9C, and 10C, the insert 30 slightly rises on one side (−Z side) in the first direction with respect to the cup 20. At this time, the insert 30 is allowed to move towards one side in the first direction by an amount of the gap 61 provided in the coupling portion 60.

When the femoral implant 12 pivots in the other direction (counterclockwise direction viewed from the +X side) about the pivotal axis AX2, the artificial hip joint 10 operates in the same way as the above-described operation of the artificial hip joint 10 except that it operates symmetrically in the third direction Y across the central axis AX1. The case where the femoral implant 12 pivots in the other direction about the pivotal axis AX2 corresponds to, for example, a case where the patient wearing the artificial hip joint 10 has his hip joint flexed and medially rotated as shown in FIG. 2. As described above, the artificial hip joint 10 of the present embodiment operates in accordance with the motion of the hip joint of the patient who wears.

Figure 11:
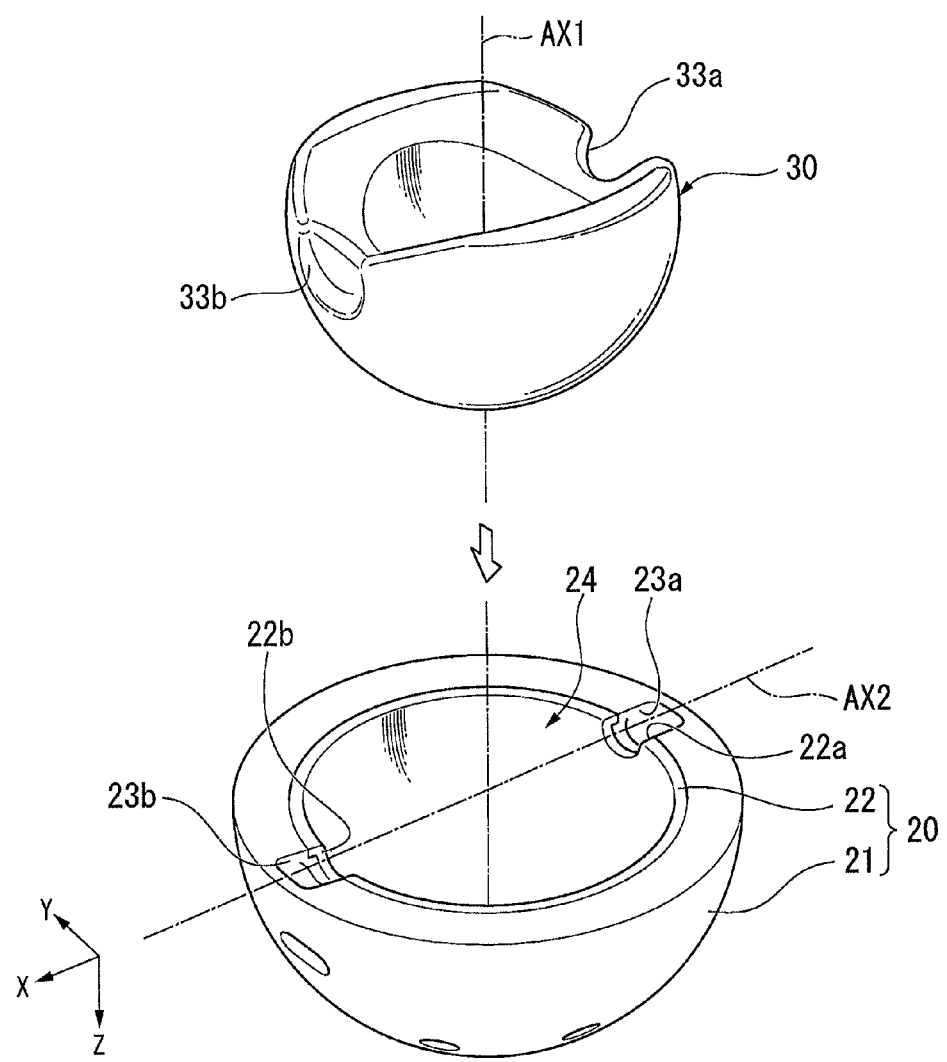
FIG. 11 is a perspective view showing a part of an assembly procedure of the artificial hip joint of the first embodiment.
Figure 12:
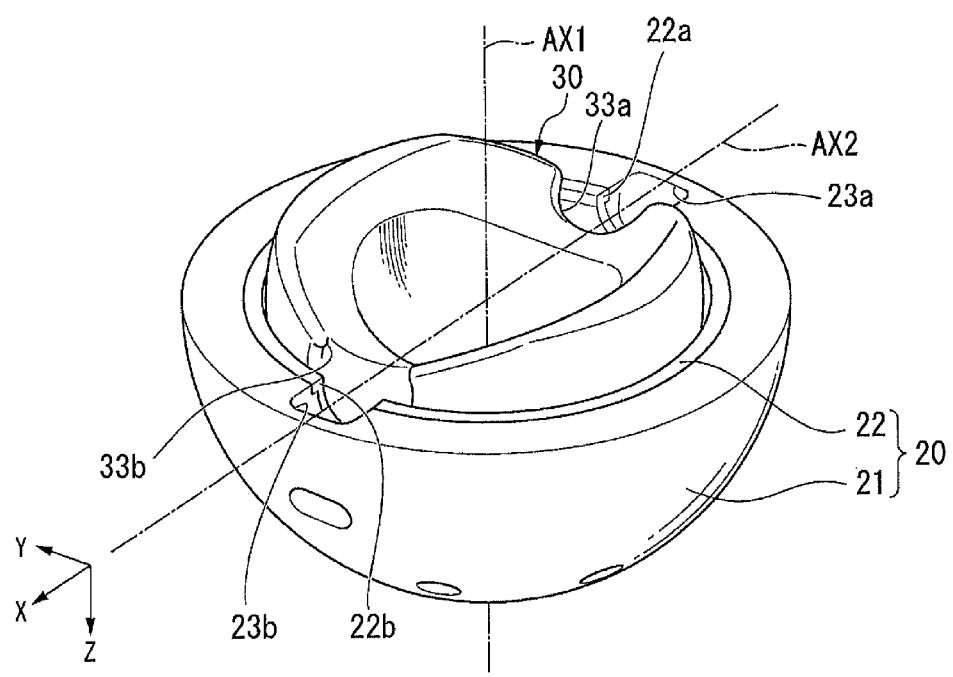
FIG. 12 is a perspective view showing a part of the assembly procedure of the artificial hip joint of the first embodiment.

Next, the assembly procedure of the artificial hip joint 10 with progression of surgery for attaching the artificial hip joint 10 to the patient will be described. FIG. 11 and FIG. 12 are perspective views showing a part of the assembly procedure of the artificial hip joint 10. FIGS. 13A-13D are sectional views showing a part of the assembly procedure of the artificial hip joint 10.

First, as shown in FIG. 2 and FIG. 3, the practitioner fixes the cup body portion 21 to the pelvic acetabulum PA. In the present embodiment, the practitioner fixes the cup body portion 21 by, for example, screwing the screws into the pelvic acetabulum PA via the screw insertion bores 21a and 21b of the cup body portion 21. At this time, it is the same as a normal artificial hip joint to pay attention so as to have an appropriate abduction angle and anteversion angle.

Further, in the cup body portion 21 of the present embodiment, attention should also be paid to the direction in which the pivot support shaft insertion holes 23a and 23b are aligned side by side. Specifically, the cup body portion 21 is fixed to the pelvic acetabulum PA so that the two pivot support shaft insertion holes 23a and 23b are aligned in a direction substantially orthogonal to the anteroposterior direction of the body and are arranged on a slightly posterior side of the craniad side in the superoinferior direction of the body and a slightly anterior side of the caudal side in the superoinferior direction of the body, respectively, on the circumference of the hole of the pelvic acetabulum PA in which the cup body portion 21 is embedded.

Then, the practitioner inserts the sliding surface component 22 into the cup body portion 21. At this time, the practitioner orients the two pivot support shaft insertion holes 23a and 23b of the cup body portion 21 and the two notch portions 22a and 22b of the sliding surface component 22 so as to be aligned facing each other, and inserts the sliding surface component 22 into the cup body portion 21.

Next, as shown in FIG. 11 and FIG. 12, the practitioner brings the insert 30 close to the cup 20 from one side (−Z side) in the first direction and inserts it into the first housing portion 24 of the cup 20. In the actual surgery, it is possible to adopt a method in which the insert 30 is reduced together with the bone head portion 12a in the cup 20 by putting the insert 30 on the bone head portion 12a of the femoral implant 12 having already been provided in the femur and performing a joint reduction operation.

Thereafter, the practitioner adjusts the posture of the insert 30 by appropriately rotating the insert 30 about the central axis AX1 so that the bearing recesses 33a and 33b of the insert 30 and the pivot support shaft insertion holes 23a and 23b of the cup 20 are aligned facing each other. By adjusting the posture of the insert 30 in this manner, in the present embodiment, the protrusion portions 32a and 32b are aligned side by side in substantially the anteroposterior direction of the body.

It is desirable that the protrusion portions 32a and 32b are aligned to a position where the neck portion 12b and the cup 20 are likely to collide in a surgical case. In terms of clinical observation, the collision position between the neck portion 12b and the cup 20 is the anterior craniad side of the cup 20 in a posterior dislocation and the posterior caudal side of the cup 20 in an anterior dislocation. Therefore, it is effective to arrange the protrusion portions 32a and 32b of the insert 30 so as to be also positioned on the anterior craniad side and the posterior caudal side of the cup 20.

Figure 13:
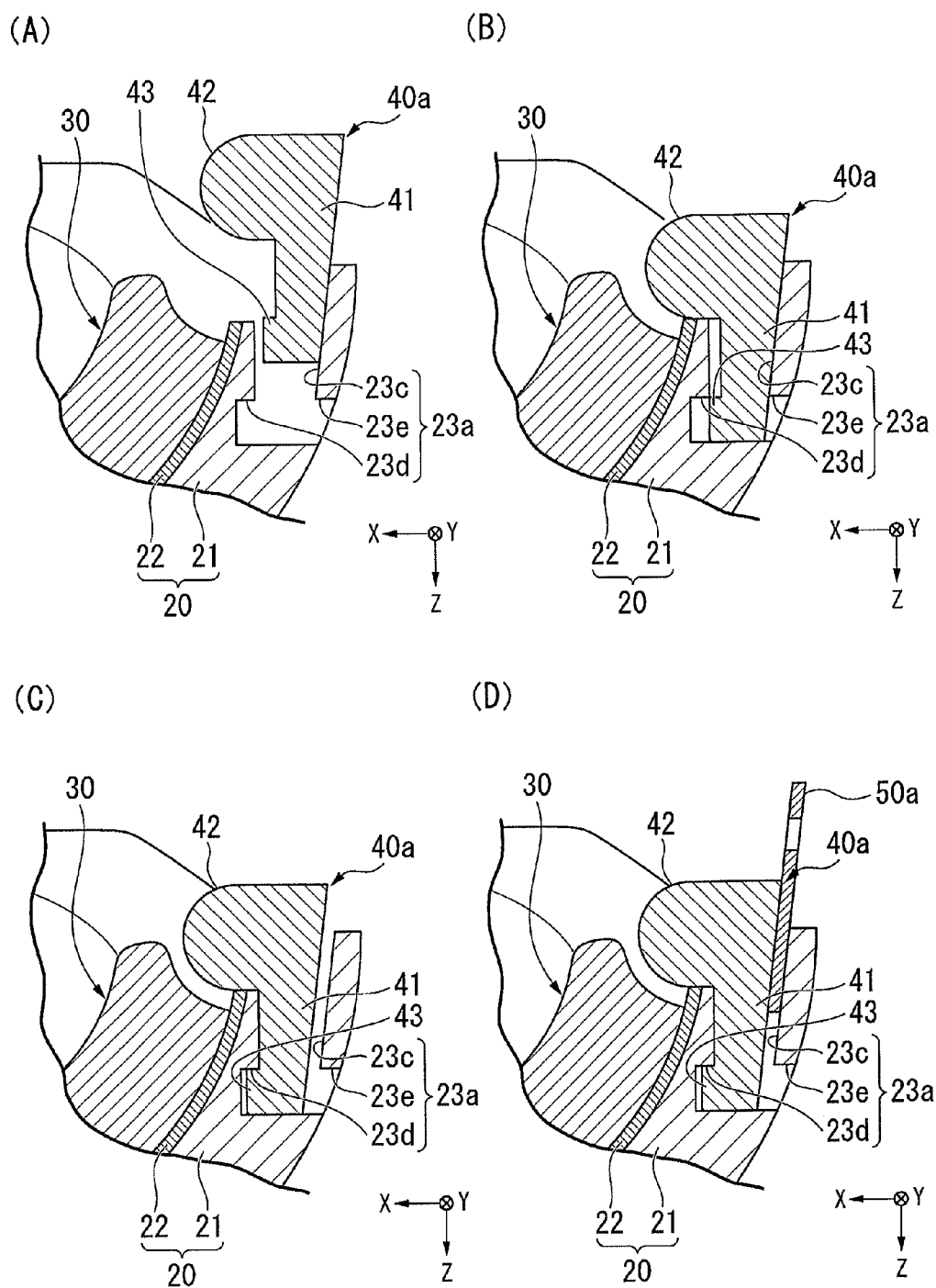
FIGS. 13A-13D are sectional views showing a part of the assembly procedure of the artificial hip joint of the first embodiment.

Next, as shown in FIGS. 13A and 13B, the practitioner inserts the pivot support shaft 40a into the pivot support shaft insertion hole 23a. Then, as shown in FIG. 13C, the practitioner moves the pivot support shaft 40a to the second direction inner side, and inserts and engages the engagement protrusion 43 into the engagement portion 23d. As shown in FIG. 13D, the practitioner fixes the support shaft fastener 50a by inserting it into a gap between the pivot support shaft 40a and the pivot support shaft insertion hole 23a, which is generated by moving the pivot support shaft 40a to the second direction inner side. Due to this, the pivot support shaft 40a is fixed to the cup 20. In the same manner as the pivot support shaft 40a, the practitioner inserts the pivot support shaft 40b into the pivot support shaft insertion hole 23b, and thus fixes it to the cup 20 with the support shaft fastener 50b. It is to be noted that the method of fixing the support shaft fasteners 50a and 50b is not particularly limited.

As the above, the assembly of the artificial hip joint 10 of the present embodiment is completed, and the operation of attaching the artificial hip joint 10 to the patient is completed. According to the present embodiment, it is possible to obtain the artificial hip joint 10 capable of sufficiently suppressing dislocation while ensuring the range of motion of the joint. This will be described in detail below.

FIGS. 30A-30C and 31A-31C are sectional views schematically showing an artificial hip joint 510 of Comparative Example 1. As shown in FIGS. 30A-30C and FIGS. 31A-31C, a cup 520 of the artificial hip joint 510 is provided with a high wall 522 protruding from a cup main body 521 to one side (−Z side) in the first direction. That is, the cup 520 is a fixed high wall type cup. As shown in FIG. 30, in the artificial hip joint 510, when the femoral implant 12 pivots in one direction (clockwise direction as viewed from the +X side) about the pivotal axis AX2, the high wall 522 is positioned on the side (left side in the figure) where the bone head portion 12*a* is about to deviate even if the bone head portion 12*a* rises, after the neck portion 12*b* comes into contact with an edge portion of the cup 520. Therefore, the high wall 522 serves as a breakwater, thereby suppressing the dislocation.

Figure 31:
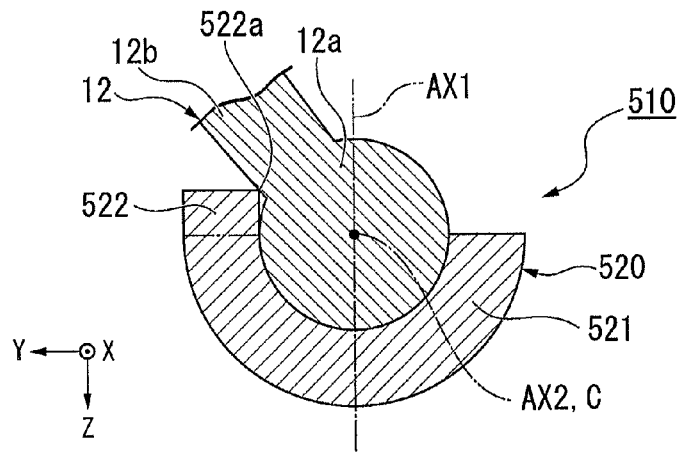
FIGS. 31A-31C are sectional views schematically showing the artificial hip joint of Comparative Example 1.
Figure 31:
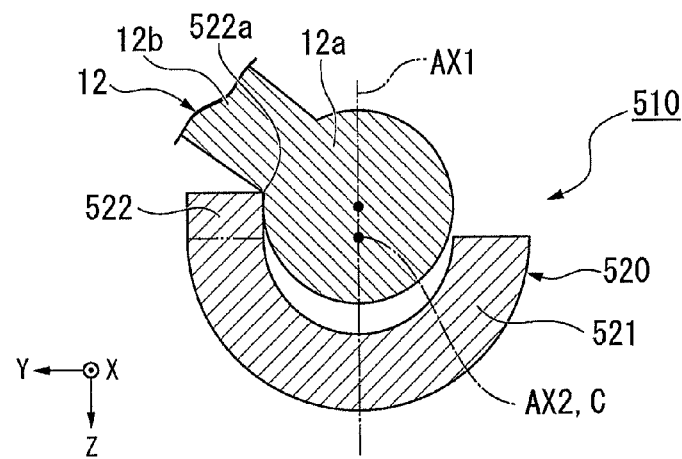
Figure 31:
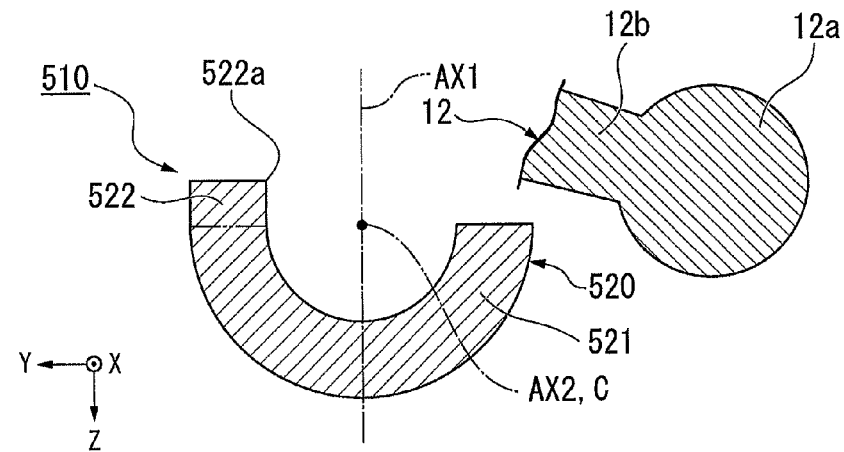

However, as shown in FIGS. 31A-31C in the artificial hip joint 510, when the femoral implant 12 pivots in the other direction (counterclockwise direction viewed from the +X side) about the pivotal axis AX2, the neck portion 12*b* comes into contact with an edge portion 522*a* of the high wall 522 with a relatively small pivot angle, and hence the pivot of the femoral implant 12 is blocked. If the femoral implant 12 is to be further pivoted in this state, the bone head portion 12*a* rises with the edge portion 522*a* as a fulcrum, and easily deviates to the side (right side in the figure) opposite to the side on which the high wall 522 is provided. Accordingly, in the artificial hip joint 510 of Comparative Example 1, while dislocation towards the side on which the high wall 522 is provided can be suppressed, dislocation towards the side opposite to the side on which the high wall 522 is provided is liable to occur.

Even in the case where dislocation does not occur, the neck portion 12*b* comes into contact with the edge portion 522*a* of the high wall 522 with a relatively small pivot angle, and hence there is also a problem of narrowing the range of motion of the joint in the other direction about the pivotal axis AX2 in the femoral implant 12. The larger the protrusion height of the high wall 522 becomes, the larger these problems become. Accordingly, it is difficult to increase the protrusion height of the high wall 522, and as a result, the dislocation suppression effect to the side on which the high wall 522 is provided is also difficult to sufficiently obtain. While, for example, it is considered to provide the high wall 522 on both sides in the third direction Y, in this case, the pivot angle becomes small in any direction about the pivotal axis AX2, and hence there is a problem that the range of motion of the joint of the artificial hip joint becomes narrower.

In response to the above problem, according to the present embodiment, as shown in FIGS. 10A-10C, even if the femoral implant 12 is further pivoted after the neck portion 12*b* comes into contact with the edge portion 32*c* in the protrusion portion 32*a* of the insert 30, the protrusion portion 32*a* is pushed into the first housing portion 24 by the neck portion 12*b*, and thus the entire insert 30 pivots. Therefore, it is difficult for the bone head portion 12*a* to rise with the edge portion 32*c* as a fulcrum. In addition, a decrease of the range of motion of the femoral implant 12 attributable to the provision of the insert 30 is unlikely to occur, and hence the pivot angle of the femoral implant 12 can be increased. Therefore, it is possible to widen the range of motion of the joint in the artificial hip joint 10. Further, as the insert 30 pivots, on the top side (the left side in the figure) of the bone head portion 12*a*, the protrusion portion 32*b* on the opposite side in the insert 30 rises from the cup 20 towards one side (−Z side) in the first direction. Therefore, the protrusion portion 32*b* functions as a breakwater, and it is possible to suppress the bone head portion 12*a* from deviating to the top side.

While FIGS. 10A-10C present the case where the femoral implant 12 pivots in one direction (clockwise direction viewed from the +X side) about the pivotal axis AX2, the above effect is obtained similarly in a case where the femoral implant 12 pivots in the other direction (counterclockwise direction viewed from the +X side) about the pivotal axis AX2. That is, in the case where the protrusion portion 32*b* is pushed into the first housing portion 24 by the neck portion 12*b*, the protrusion portion 32*a* protrudes and functions as a breakwater.

Figure 32:
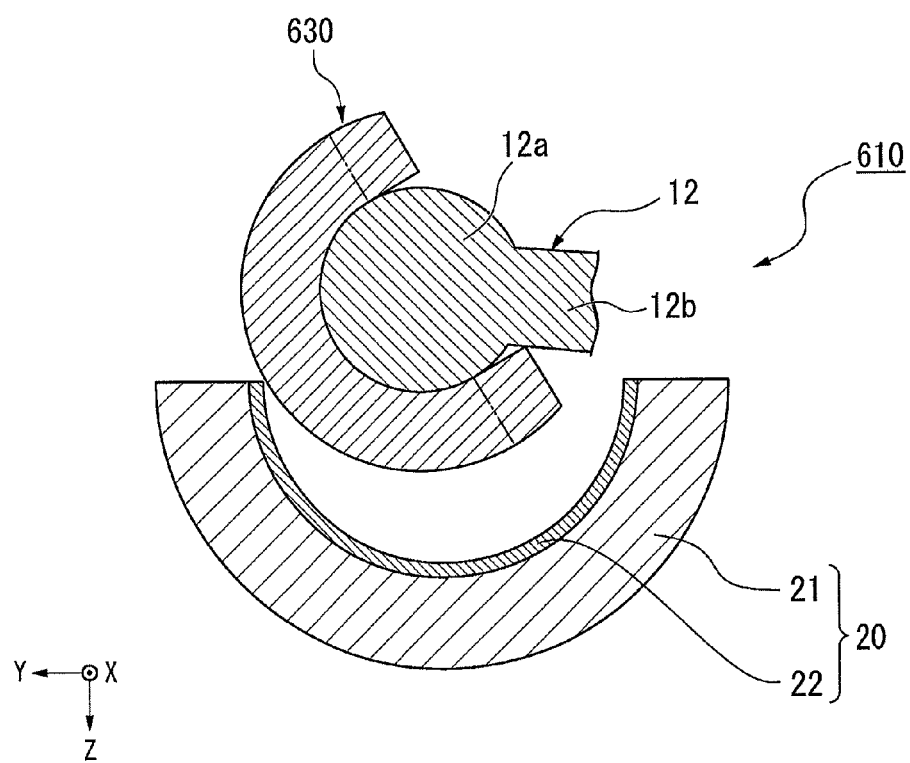
FIG. 32 is a sectional view schematically showing an artificial hip joint of Comparative Example 2.

Further, according to the present embodiment, since the coupling portion 60 that couples the insert 30 to the cup 20 is provided, it is possible to suppress the insert 30 from coming off from the cup 20. This point is one of the most important points in the present embodiment. It is because unless the coupling portion 60 is provided, an insert 630 and the femoral implant 12 cannot be suppressed from dislocating from the cup 20 integrally as in an artificial hip joint 610 of Comparative Example 2 shown in FIG. 32.

The artificial hip joint 610 of Comparative Example 2 is different from the artificial hip joint 10 of the present embodiment in that the coupling portion 60 is not provided. In the artificial hip joint 610, even if a part of the insert 630 protrudes due to pivot of the femoral implant 12, it is impossible to suppress the insert 630 itself from coming off from the cup 20, and it is hence impossible to cause the protruding part of the insert 630 to function as a breakwater. Accordingly, unlike the insert 30 of the present embodiment, by putting the insert 630 on the bone head portion 12*a*, the insert 630 in the artificial hip joint 610 only obtains a dislocation suppression effect to an extent that the insert 630 is caused to function as a large-diameter bone head of the diameter of the insert 630, thereby failing to obtain a sufficient dislocation suppression effect. In other words, the insert 630 in the artificial hip joint 610 not provided with the coupling portion 60 is totally different in function of contributing to dislocation suppression from the insert 30 of the present embodiment, and not capable of giving a sufficient dislocation suppression effect. In this respect, the artificial hip joint 610 of Comparative Example 2 is totally different from the artificial hip joint 10 of the present embodiment.

As described above, according to the present embodiment, even when the femoral implant 12 pivots in any direction about the pivotal axis AX2, the insert 30 pivots with respect to the cup 20, thereby ensuring the range of motion of the joint and causing the portion of the insert 30 protruding more to one side (−Z side) in the first direction than the cup 20 by the pivot to function as a breakwater. Further, the insert 30 can also be suppressed from deviating from the cup 20 by the coupling portion 60. Accordingly, it is possible to realize the artificial hip joint 10 capable of sufficiently suppressing dislocation while ensuring the range of motion of the joint.

In the case where the femoral implant 12 pivots about an axis parallel to the third direction Y, the protrusion portion 32 is not provided on the side where the neck portion 12*b* moves, and it is hence possible to sufficiently increase the pivot angle at which the neck portion 12b comes into contact with the edge portion of the insert 30 or the edge portion of the cup 20. This makes it possible to ensure the range of motion of the joint of the artificial hip joint 10 also about the axis parallel to the third direction Y.

In other words, the operational effect of the present embodiment described above is as follows: by adopting a structure in which the insert 30 having the two protrusion portions 32 is capable of pivoting motion without deviating from the cup 20, the neck portion 12b or the like, which is an femoral element pushes down one of the protrusion portions 32 of the insert 30 in a position where dislocation is imminent, and hence a pivoting motion of the insert 30 is caused to occur, and the other one of the protrusion portions 32 rising on the top side of the bone head portion 12a serves as a breakwater for dislocation of the bone head portion 12a, thereby suppressing dislocation.

Next, the operational effect of the present embodiment will be described in more detail regarding the case in which the artificial hip joint 10 of the present embodiment described above is placed inside the human body. First, major motions causing an artificial hip joint to dislocate include two motions of flexion and medial rotation of the hip joint (Motion A) and extension and lateral rotation of the hip joint (Motion B). In Motion A, the neck portion approaches and comes into contact with the anterior of the cup. After that, the bone head portion rises and the bone head portion deviates towards the posterior of the cup, thereby causing so-called posterior dislocation. In Motion B, the neck portion approaches and comes into contact with the posterior of the cup. After that, the bone head portion rises and the bone head portion deviates towards the anterior of the cup, thereby causing so-called anterior dislocation.

As described above, the artificial hip joint 10 of the present embodiment is attached to the body such that the protrusion portions 32a and 32b are aligned side by side along substantially the anteroposterior direction of the body. Therefore, as shown in FIG. 2, in the case of the hip joint flexion and medial rotation (Motion A), the neck portion 12b of the femoral implant 12 approaches the anterior craniad side of the cup 20 and pushes into the cup 20 the protrusion portion 32b positioned in the portion of the anterior craniad side of the insert 30. As a result, the insert 30 pivots, and the protrusion portion 32a positioned in the portion of the posterior caudal side of the insert 30 protrudes. Conventionally, in a position where the hip joint is flexed and medially rotated, the bone head portion is likely to dislocate in a direction of deviating to the posterior caudal side of the cup. However, in the present embodiment, the protrusion portion 32a protruding suppresses dislocation of the bone head portion 12a.

On the other hand, as shown in FIG. 3, in the case of the hip joint extension and lateral rotation (Motion B), the neck portion 12b of the femoral implant 12 approaches the posterior caudal side of the cup 20 and pushes into the cup 20 the protrusion portion 32a positioned in the portion of the posterior caudal side of the insert 30. As a result, the insert 30 pivots, and the protrusion portion 32b positioned in the portion of the anterior craniad side of the insert 30 protrudes. Conventionally, in a position where the hip joint is extended and laterally rotated, the bone head portion is likely to dislocate in a direction of deviating to the anterior craniad side of the cup. However, in the present embodiment, the protrusion portion 32b protruding suppresses dislocation of the bone head portion 12a.

As the above, the artificial hip joint 10 of the present embodiment has a sufficient dislocation suppression effect for both the anterior dislocation and the posterior dislocation in the human body at the same time.

Here, for example, suppression of dislocation in all directions is considered. In this case, it is conceivable that the insert can be pivoted in any direction with respect to the cup, so that the femoral implant pivots and a part opposite to a part where the insert is pushed into protrudes. However, it is very difficult to provide a coupling portion that couples the insert to the cup while realizing such a configuration. Accordingly, in the case of such a configuration, for example, it has the same configuration as the artificial hip joint 610 of Comparative Example 2 without a the coupling part shown in FIG. 32, the insert cannot be suppressed from deviating from the cup, resulting in failing to cause the insert to have a function as a breakwater. Therefore, dislocation cannot be sufficiently suppressed.

The above-mentioned anterior dislocation and posterior dislocation are clinically problematic, and it is particularly important to suppress these two types of dislocations in substantially opposite directions. On the other hand, dislocation in other directions, that is, for example, a left and right direction is less likely to occur compared with anterior dislocation and posterior dislocation, and there is little need to impart a function to protrude a part of the insert into a breakwater. Therefore, in the present embodiment, it is configured that the part of the insert 30 protrudes in the direction in which dislocation is likely to occur so that dislocation can be suppressed by providing the coupling portion 60 that couples the insert 30 to the cup 20 so as to be pivotable about the pivotal axis AX2 along the direction in which dislocation hardly occurs.

In this manner, in the present embodiment, it is sufficient to couple the insert 30 to the cup 20 so as to be pivotable about one axis, so that it is possible to easily provide the coupling portion 60 by the above-described recess and projection fitting structure or the like. Hence, according to the present embodiment, it is possible to preferably suppress dislocation while satisfying the clinical requirement by providing the pivotal axis AX2 in a direction orthogonal to a direction in which dislocation suppression is highly necessary while arranging the protrusion portions 32a and 32b along the direction in which dislocation suppression is highly necessary.

In other words, the operational effect described above is as follows. In the case of the artificial hip joint 610 of Comparative Example 2, since the coupling portion 60 is not provided, the insert 630 can be pivoted in any direction, for example. However, on the other hand, since the entire insert 630 easily deviates from the cup 20 and the insert 630 cannot be used as a breakwater, the dislocation suppression effect cannot be sufficiently obtained. On the other hand, in the present embodiment, it is configured to limit the direction in which the insert 30 pivots on the basis of the direction in which dislocation is likely to occur and the direction in which dislocation is unlikely to occur and to provide the coupling portion 60 capable of suppressing the insert 30 from deviating from the cup 20. Due to this, in the present embodiment, as compared with the artificial hip joint 610 of Comparative Example 2, it is possible to greatly improve the dislocation suppression effect and to achieve both ensuring of the range of motion of the joint and the sufficient dislocation suppression effect.

Further, according to the present embodiment, the coupling portion 60 has the recess and projection fitting structure of the bearing recesses 33a and 33b and the shaft body portion 42 of the pivot support shafts 40a and 40b. Therefore, the configuration of the coupling portion 60 can be simplified.

Further, according to the present embodiment, since the protrusion portions 32a and 32b are provided, it is possible to increase the protrusion height of the portion of the insert 30 protruding by a part thereof being pushed into by the neck portion 12b. As a result, it is possible to improve the function as a breakwater by the protruding part of the insert 30, and to further suppress dislocation.

Further, according to the present embodiment, the recess and projection fitting structure of the coupling portion 60 is a loose fitting. Therefore, the insert 30 is coupled to the cup 20 with some backlash, and motion in the first direction Z is allowed. Due to this, the motion in a direction in which the insert 30 and the bone head portion 12a integrally rise from the cup 20 and about to dislocate as shown in FIG. 8C, FIG. 9C, and FIG. 10C is allowed by the amount of the backlash. Specifically, the movement of the insert 30 is allowed until the inner side surfaces of the bearing recesses 33a and 33b come into contact with the shaft body portion 42 of the pivot support shafts 40a and 40b. Accordingly, as shown in FIG. 8C, FIG. 9C, and FIG. 10C, the pivot angle of the femoral implant 12 can be increased more and the range of motion of the joint of the artificial hip joint 10 can be widened more.

Also, for example, in an artificial hip joint having a restraint type cup, collision between the neck portion and the cup margin is likely to occur frequently. In addition, since it is a joint connection that is too strong to allow deviation of the bone head portion, the load applied to the restraint type cup and the femoral implant is great in a case where a force is applied to the femoral implant in a direction where the bone head portion is drawn out from the restraint type cup. Therefore, in an artificial hip joint having a restraint type cup, damage of the restraint type cup and the femoral implant, loosening of the boundary between the restraint type cup and the pelvic acetabulum, and loosening of the boundary between the femoral implant and the femur are likely to occur in an early postoperative period. Thus, the artificial hip joint having a restraint type cup has a problem of low durability.

On the other hand, according to the present embodiment, the opening of the second housing portion 34 of the insert 30 has a size equal to or larger than the maximum cross-section of the bone head portion 12a. Therefore, it is possible to freely perform insertion and deviation of the bone head portion 12a into and from the second housing portion 34. This is totally different from that the restraint type cup has a dislocation suppression function by disabling the deviation of the bone head portion by a narrow opening. Due to such a configuration that allows insertion and deviation of the bone head portion 12a into and from the insert 30, the load applied to the cup 20 and the femoral implant 12 can be reduced even if a force is applied to the femoral implant 12 in a direction where the bone head portion 12a is drawn out from the insert 30. Accordingly, in the artificial hip joint 10 of the present embodiment, damage of the cup 20 and the femoral implant 12 can be suppressed, and the occurrence of loosening of the boundary between the cup 20 and the pelvic acetabulum PA can be suppressed. In addition, loosening of the boundary between the femoral implant 12 and the femur can also be suppressed. As a result, the durability of the artificial hip joint 10 can be improved as compared with the artificial hip joint having the restraint type cup.

In general, there is little possibility of dislocation with a force in a direction where the bone head portion 12a is drawn out from the insert 30 as in pulling the lower extremity, and a short-distance deviation and restoration of the bone head portion 12a due to a draw-out external force are considered to be safe motions. Accordingly, with the configuration that allows the insertion and deviation of the bone head portion 12a with respect to the insert 30, it is possible to preferably obtain a necessary dislocation suppression effect while reducing the load applied to the cup 20 and the femoral implant 12.

In the present embodiment, the insert 30 pivots when the neck portion 12b further pivots from the state in which the neck portion 12b is in contact with the edge portion 32c of the insert 30 as described above. Due to this, even if the neck portion 12b makes contact with the insert 30, application of a load to the cup 20 and the femoral implant 12 can be further suppressed. This can further suppress the cup 20 and the femoral implant 12 from being damaged, and can further suppress the loosening of the boundary between the cup 20 and the pelvic acetabulum PA and the loosening of the boundary between the femoral implant 12 and the femur from occurring. Accordingly, the durability of the artificial hip joint 10 can be further improved.

Further, in the present embodiment, as described above, the motion of the insert 30 and the bone head portion 12a integrally rising from the cup 20 and about to dislocate is allowed to some extent. For this reason, even in a case where the femoral implant 12 further pivots after the neck portion 12b comes into contact with the edge portion of the cup 20, it is possible to reduce the burden imposed on the boundary between the cup 20 and the pelvic acetabulum PA and the burden imposed on the femoral implant 12 and the femur.

According to the present embodiment, the sliding surface component 22 is provided, and the inside of the sliding surface component 22 is the first housing portion 24 in which the insert 30 is housed. Therefore, even if the inner side surface 21d of the cup body portion 21 is provided with recess and projection by the screw insertion bores 21a and 21b for the purpose of fixing the cup body portion 21 to the pelvic acetabulum PA as in the present embodiment, it is possible to make the inner side surface of the first housing portion 24 as a sliding surface a smooth hemispherical surface. This makes it possible to reduce the friction between the insert 30 and the cup 20 caused when the insert 30 pivots, and to facilitate the insert 30 to pivot with respect to the cup 20.

Variation of First Embodiment

Figure 14:
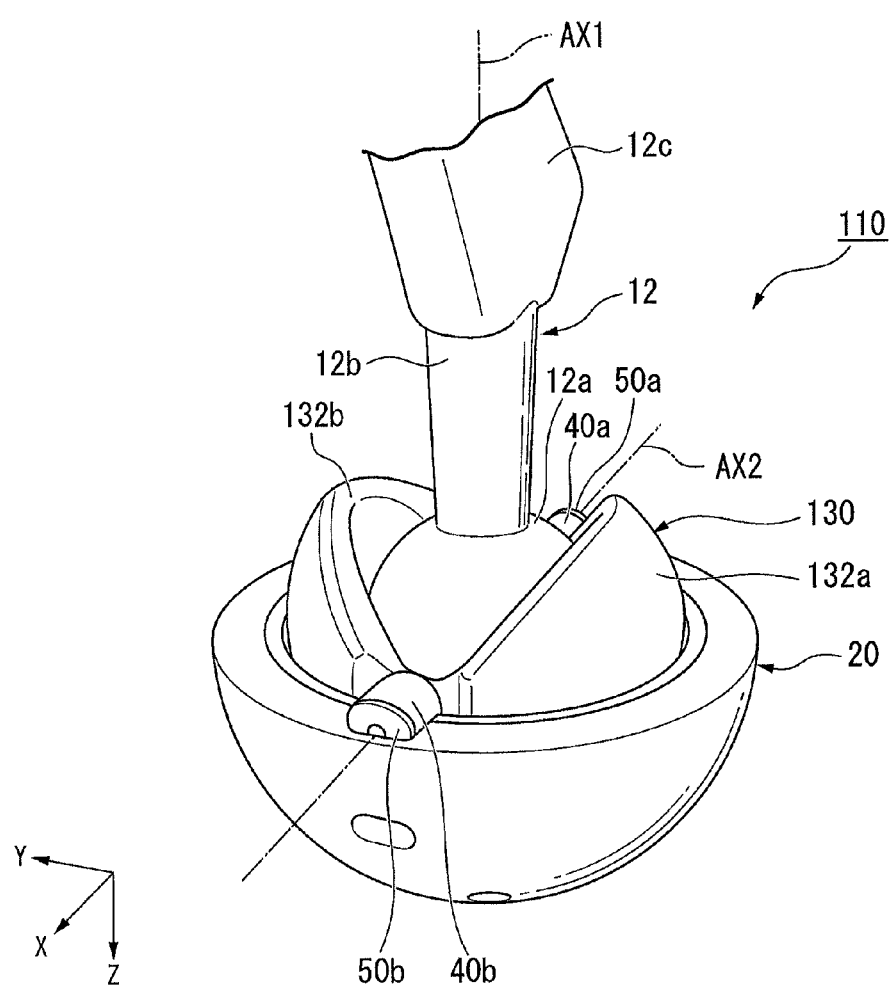
FIG. 14 is a perspective view showing an artificial hip joint that is a variation of the first embodiment.

FIG. 14 is a perspective view showing an artificial hip joint 110, which is a variation of the first embodiment. As shown in FIG. 14, in the artificial hip joint 110, the protrusion height of protrusion 132a and 132b of an insert 130 decreases from the circumferential center towards both circumferential sides. An end portion on one side (−Z side) in the first direction of the circumferential center in the protrusion portions 132a and 132b is positioned on one side in the first direction than the bone head portion 12a. Other configurations of the artificial hip joint 110 are the same as those of the artificial hip joint 10 described above.

According to the present variation, since the protrusion height of the protrusion portions 132a and 132b can be increased, an increased dislocation suppression effect can be obtained.

Second Embodiment

Figure 15:
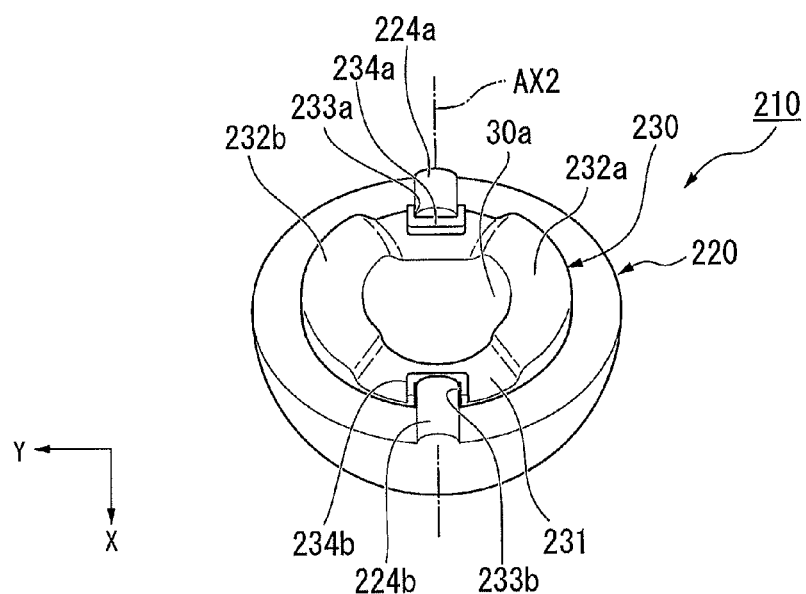
FIG. 15 is a perspective view showing an artificial hip joint of a second embodiment.
Figure 16:
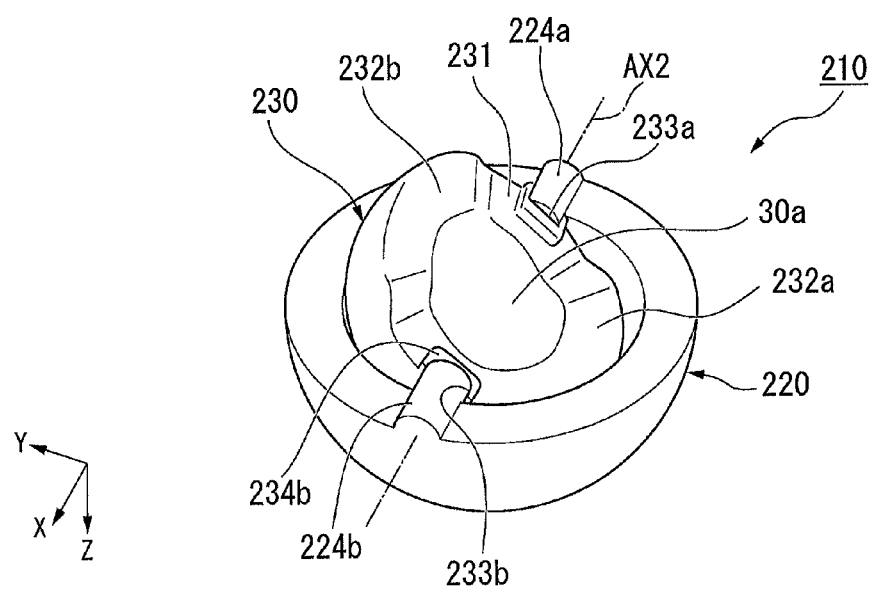
FIG. 16 is a perspective view showing the artificial hip joint of the second embodiment.
Figure 17:
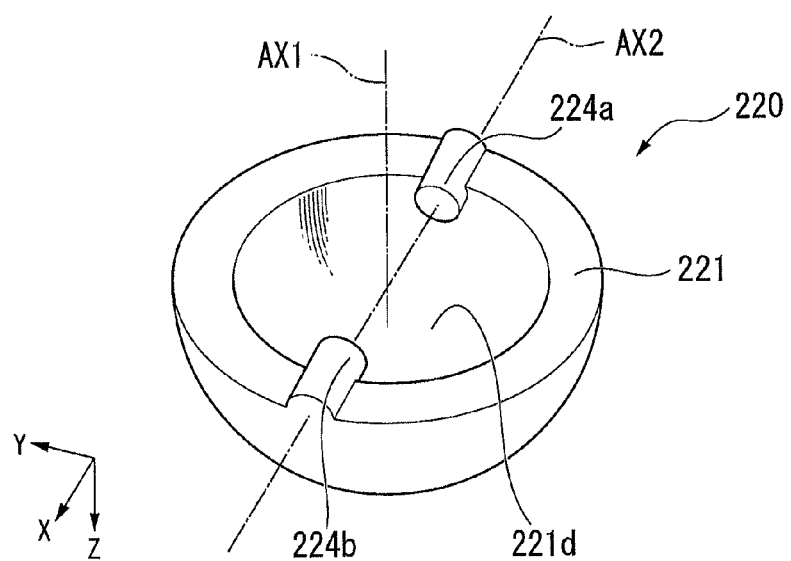
FIG. 17 is a perspective view showing a cup of the second embodiment.
Figure 18:
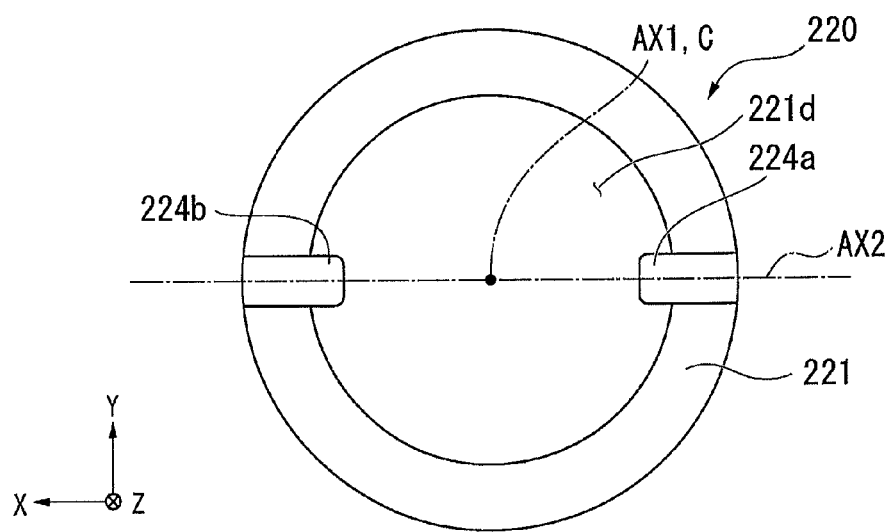
FIG. 18 is a view of the cup of the second embodiment as viewed from one side in a first direction.
Figure 19:
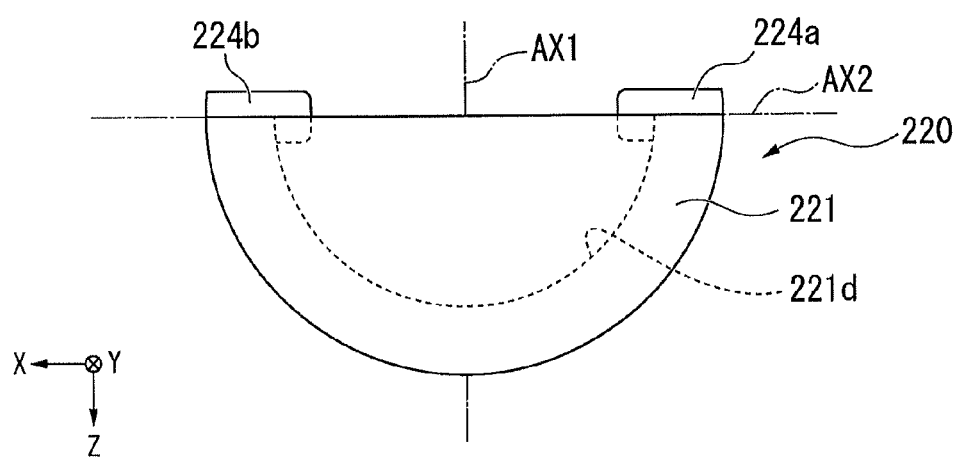
FIG. 19 is a view of the cup of the second embodiment as viewed along a third direction.
Figure 20:
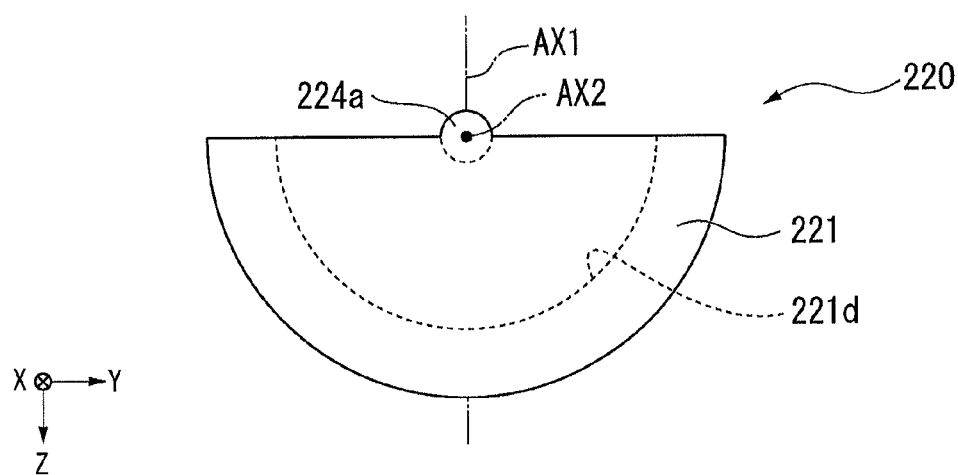
FIG. 20 is a view of the cup of the second embodiment as viewed along a second direction.
Figure 21:
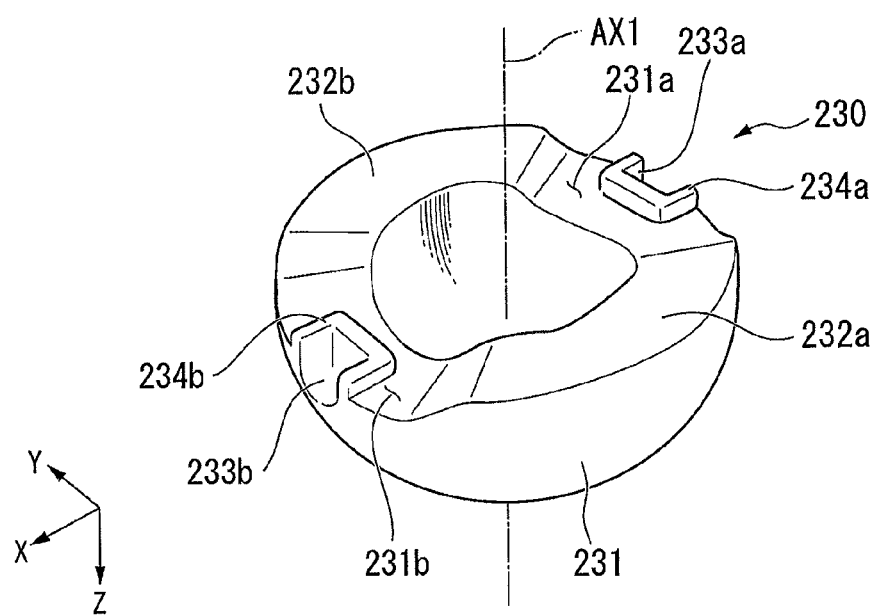
FIG. 21 is a perspective view showing an insert of the second embodiment.
Figure 22:
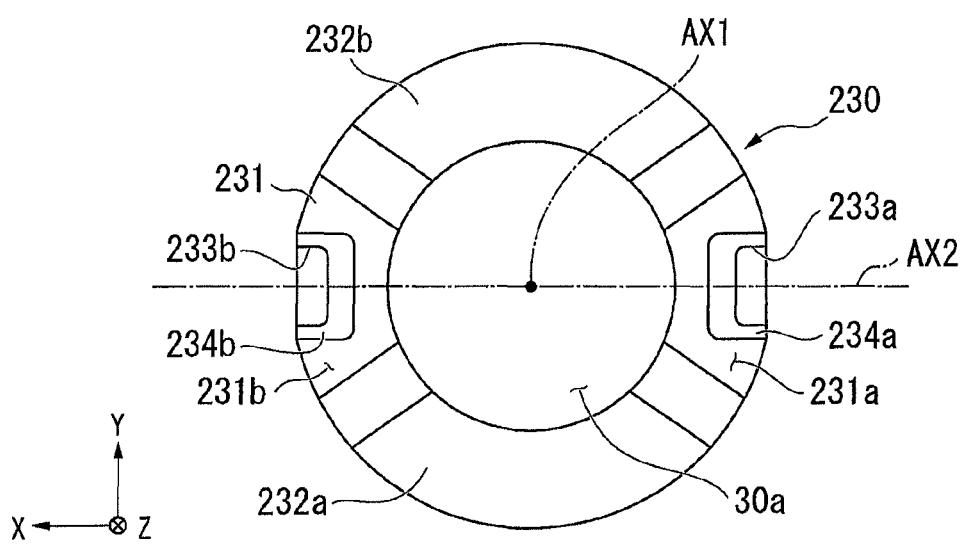
FIG. 22 is a view of the insert of the second embodiment as viewed from one side in the first direction.
Figure 23:
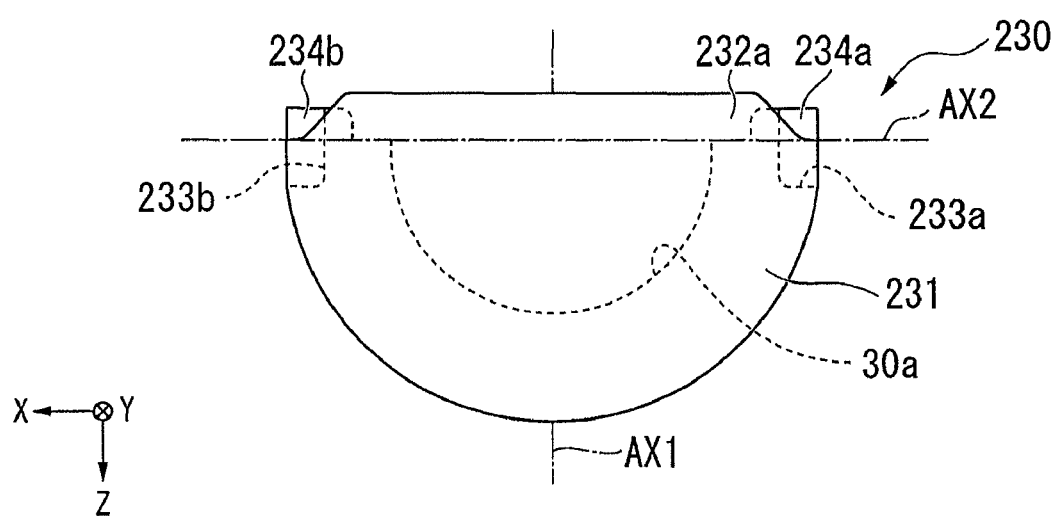
FIG. 23 is a view of the insert of the second embodiment as viewed along the third direction.
Figure 24:
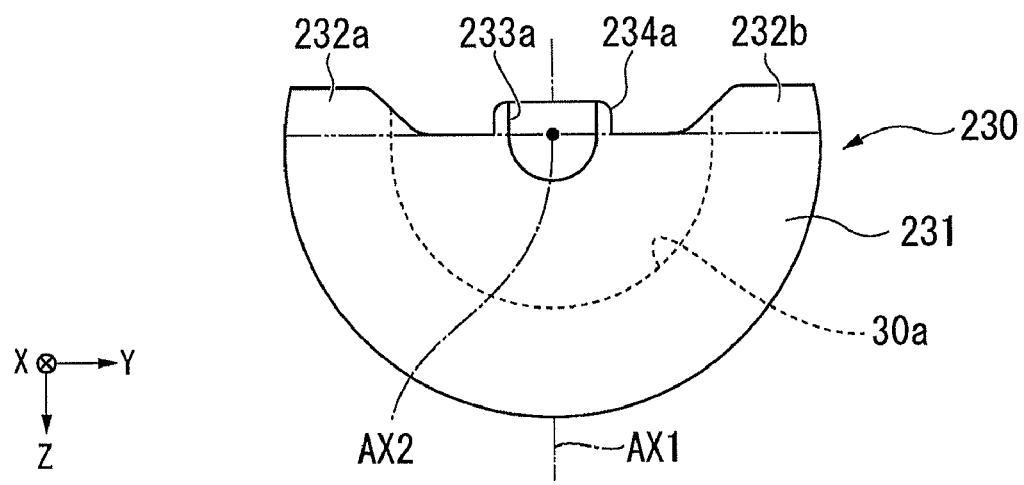
FIG. 24 is a view of the insert of the second embodiment as viewed along the second direction.

FIG. 15 and FIG. 16 are perspective views showing an artificial hip joint 210 of the present embodiment. FIG. 17 is a perspective view showing a cup 220. FIG. 18 is a view of the cup 220 viewed from one side (−Z side) in the first direction. FIG. 19 is a view of the cup 220 viewed along the third direction Y. FIG. 20 is a view of the cup 220 viewed along the second direction X. FIG. 21 is a perspective view showing an insert 230. FIG. 22 is a view of the insert 230 viewed from one side (−Z side) in the first direction. FIG. 23 is a view of the insert 230 viewed along the third direction Y. FIG. 24 is a view of the insert 230 viewed along the second direction X. FIG. 15 shows a case where the artificial hip joint 210 of the present embodiment is in the reference posture. It should be noted that the same components as those of the above embodiment are appropriately denoted by the identical reference numerals or the like, and the description thereof may be omitted.

In the present embodiment, as shown in FIG. 17 to FIG. 20, the cup 220 includes a hemispherical, shell-shaped cup body portion 221 that opens to one side (−Z side) in the first direction and cylindrical shaft portions (projection portions) 224a and 224b provided at the end portions of one side in the first direction of the cup body portion 221. The shaft portion 224a and the shaft portion 224b are arranged across the central axis AX1 in the second direction X. The shaft portion 224a and the shaft portion 224b protrude to the second direction inner side (radially inward) than the inner side surface 221d of the cup body portion 221. In the present embodiment, the cup 220 is, for example, a single member.

In the present embodiment, as shown in FIG. 21 to FIG. 24, the insert 230 includes a hemispherical, shell-shaped insert body portion 231 that opens to one side (−Z side) in the first direction and protrusion portions 232a and 232b that protrude from the insert body portion 231 towards one side in the first direction. The radial dimensions of the protrusion portions 232a and 232b are the same as the radial dimension of the wall portion of the insert body portion 231 over the entire first direction Z. The surfaces on one side in the first direction of the protrusion portions 232a and 232b are circumferentially extending flat surfaces.

As shown in FIG. 21 and FIG. 22, flat portions 231a and 231b, which are a part of the surface on one side (−Z side) in the first direction of the insert body portion 231, are provided circumferentially between the protrusion portion 232a and the protrusion portion 232b. The flat portions 231a and 231b and the surface on one side in the first direction of the protrusion portions 232a and 232b are parallel. The flat portions 231a and 231b and the surface on one side in the first direction of the protrusion portions 232a and 232b are connected to each other via inclined surfaces.

A portion on the second direction outer side at the circumferential center of the flat portion 231a is provided with a quadrangular prism-shaped bearing protrusion 234a protruding from the flat portion 231a to one side (−Z side) in the first direction. A portion on the second direction outer side at the circumferential center of the flat portion 231b is provided with a quadrangular prism-shaped bearing protrusion 234b protruding from the flat portion 231b to one side in the first direction. As shown in FIG. 23 and FIG. 24, the end portions on one side in the first direction of the bearing protrusions 234a and 234b are positioned on the other side (+Z Side) in the first direction than the end portions on one side in the first direction of the protrusion portions 232a and 232b.

In the present embodiment, as shown in FIG. 21 and FIG. 24, bearing recesses (recess portions) 233a and 233b are recessed from one side (−Z side) in the first direction to the other side (+Z side) in the first direction of the bearing protrusions 234a and 234b. The bearing recesses 233a and 233b are provided so as to astride to the insert body portion 231. The bearing recesses 233a and 233b open on the second direction outer side.

As shown in FIG. 15, the shaft portions 224a and 224b are fitted to the bearing recesses 233a and 233b, respectively. In the present embodiment, a coupling portion is constituted by the bearing recesses 233a and 233b and the shaft portions 224a and 224b. Accordingly, as shown in FIG. 16, the insert 230 is coupled to the cup 220 so as to be pivotable about the pivotal axis AX2. In the present embodiment, the gap between the bearing recesses 233a and 233b and the shaft portions 224a and 224b is sufficiently small. Even in this case, it is possible to obtain the artificial hip joint 210 capable of sufficiently suppressing dislocation while ensuring the range of motion of the joint.

Third Embodiment

Figure 25:
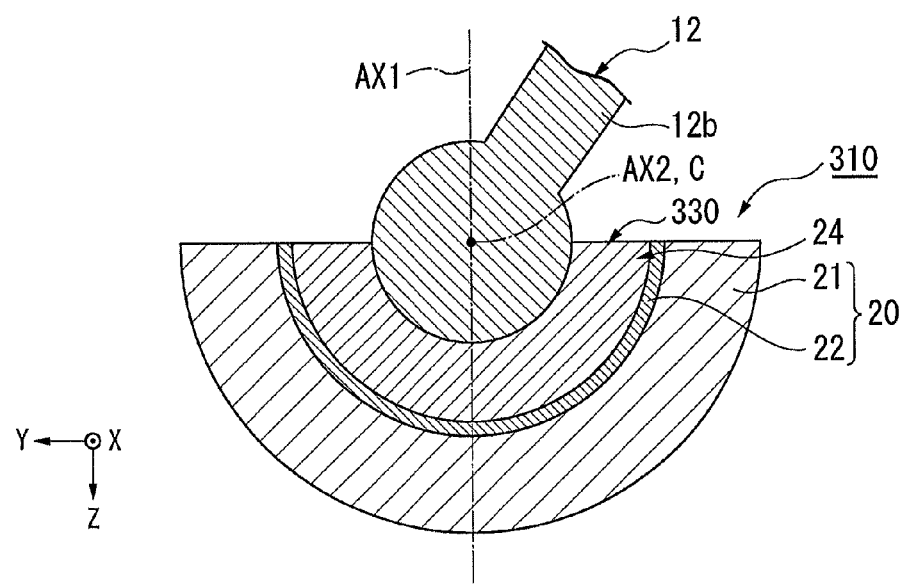
FIG. 25 is a sectional view showing an artificial hip joint of a third embodiment.
Figure 26:
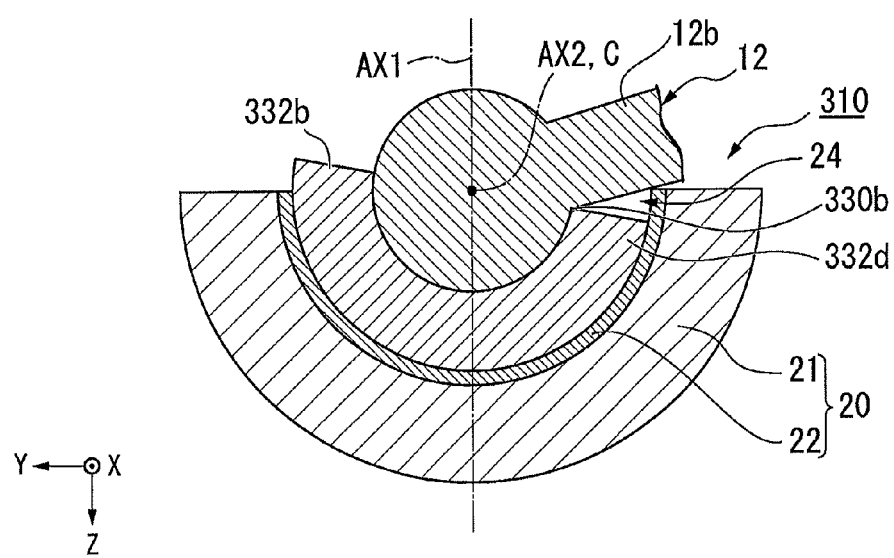
FIG. 26 is a sectional view showing the artificial hip joint of the third embodiment.

FIG. 25 and FIG. 26 are sectional views showing an artificial hip joint 310 of the present embodiment. FIG. 25 shows a case where the artificial hip joint 310 of the present embodiment is in the reference posture. It should be noted that the same components as those of the above embodiment are appropriately denoted by the identical reference numerals or the like, and the description thereof may be omitted.

In the present embodiment, as shown in FIG. 25, an insert 330 does not have the protrusion portion 32, unlike the insert 30 of the first embodiment. In the present embodiment, the insert 330 has substantially the same configuration as that of the insert body portion 31 of the first embodiment. The entire insert 330 can be housed in the first housing portion 24 of the cup 20. In the reference posture shown in FIG. 25, the surface on one side (−Z side) in the first direction of the insert 330 is arranged on the same plane as the surface on one side in the first direction of the cup 20.

As shown in FIG. 26, in the present embodiment, when the neck portion 12b pivots, an inner edge portion 330b of the insert 330 comes into contact with the neck portion 12b, and a portion 332d on one side (−Y side) in the third direction of the insert 330 is pushed into the first housing portion 24. As a result, the insert 330 pivots, and a portion 332b on the other side (+Y side) in the third direction of the insert 330 protrudes more towards one side (−Z side) in the first direction than the cup 20. Accordingly, the portion 332b functions as a breakwater similarly to the protrusion portion 32 of the first embodiment, thereby giving a dislocation suppression effect. In this manner, even in a state where the protrusion portion 32 is not provided, the artificial hip joint 310 capable of suppressing dislocation to some extent while ensuring the range of motion of the joint can be obtained.

Fourth Embodiment

Figure 27:
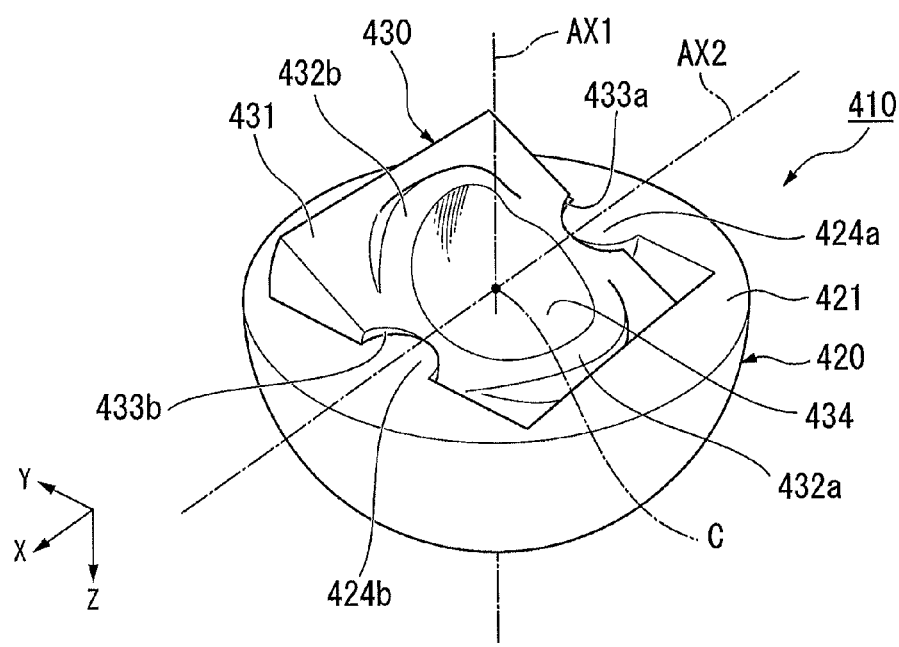
FIG. 27 is a perspective view showing an artificial hip joint of a fourth embodiment.
Figure 28:
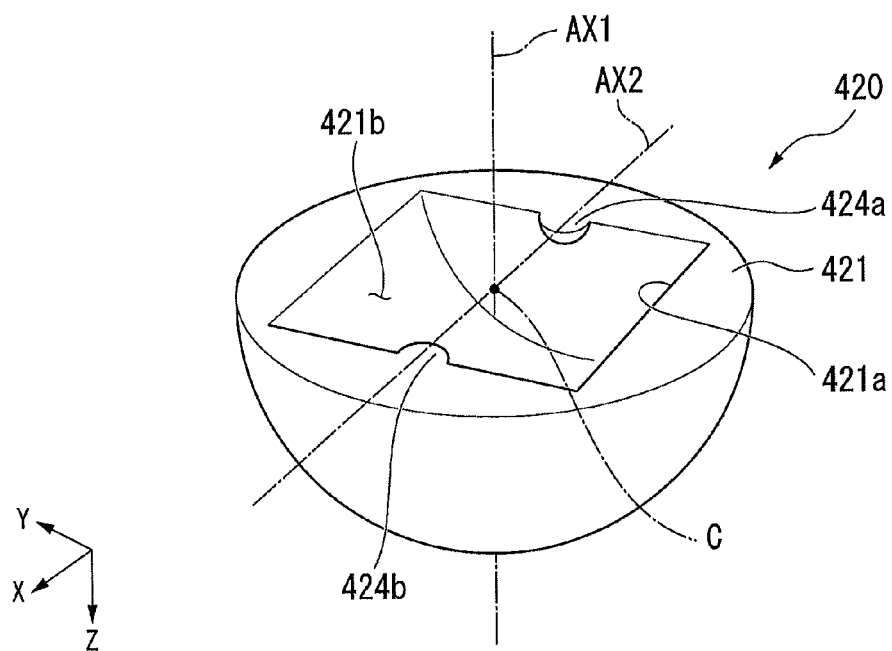
FIG. 28 is a perspective view showing a cup of the fourth embodiment.
Figure 29:
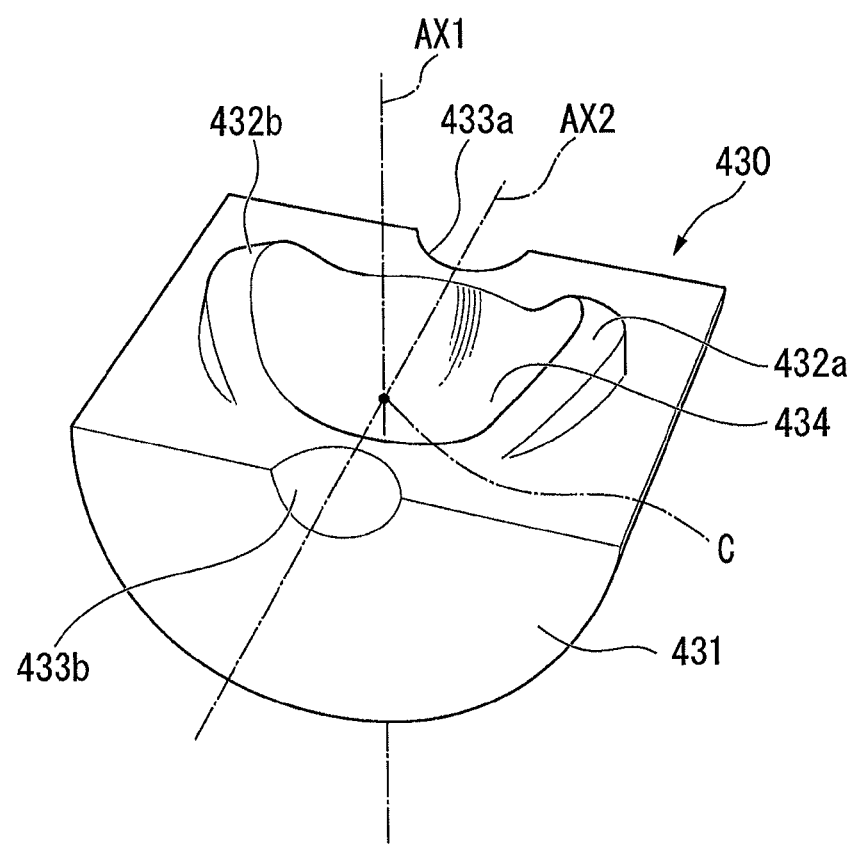
FIG. 29 is a perspective view showing an insert of the fourth embodiment.
Figure 30:
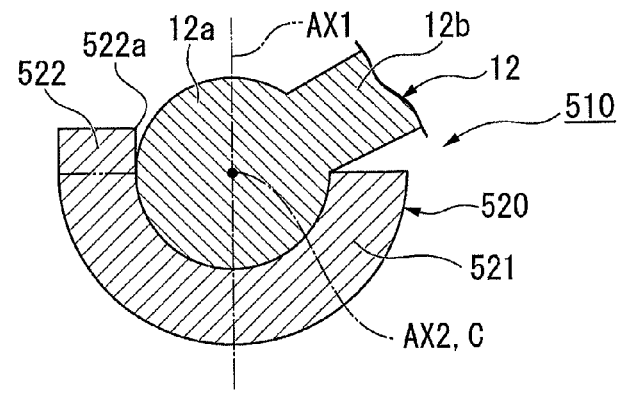
FIGS. 30A-30C are sectional views schematically showing an artificial hip joint of Comparative Example 1.
Figure 30:
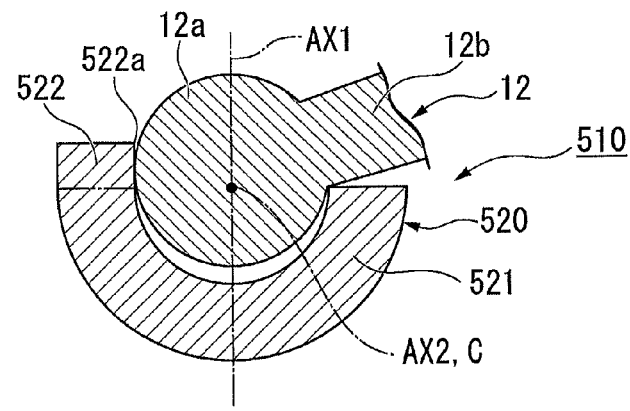
Figure 30:
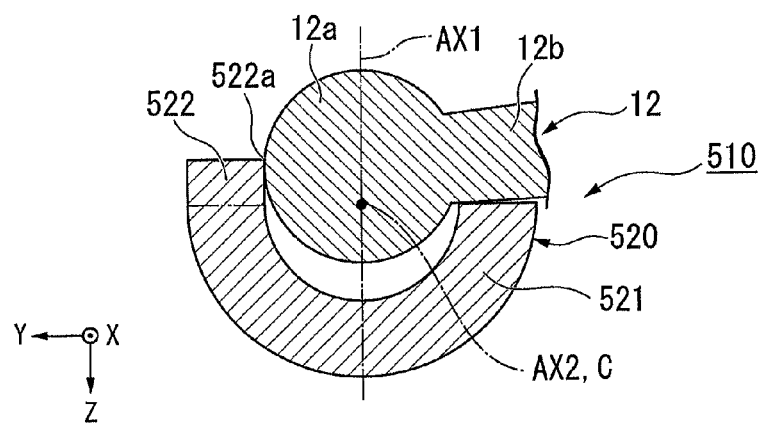

FIG. 27 is a perspective view showing an artificial hip joint 410 of the present embodiment. FIG. 28 is a perspective view showing a cup 420 of the present embodiment. FIG. 29 is a perspective view showing an insert 430 of the present embodiment. FIG. 29 shows the insert 430 in a case of the reference posture. It should be noted that the same components as those of the above embodiment are appropriately denoted by the identical reference numerals or the like, and the description thereof may be omitted.

As shown in FIG. 27 and FIG. 28, in the present embodiment, the cup 420 has a hemispherical cup body portion 421 that projects on the other side (+Z side) in the first direction and shaft portions (projection portions) 424a and 424b that protrude to the second direction inner side from the inner side surface of a first housing portion 421a provided on the cup body portion 421. The first housing portion 421a is a semi-cylindrical hole that is recessed from the surface on one side (−Z side) in the first direction of the cup body portion 421 towards the other side in the first direction, and the inside thereof extends in the second direction X. A bottom surface 421b of the first housing portion 421a is a semi-cylindrical surface and is a sliding surface on which the insert 430 slides.

In the present embodiment, as shown in FIG. 29, the insert 430 has a semi-cylindrical insert body portion 431 that extends in the second direction X and protrusion portions 432a and 432b that protrude from the insert body portion 431 towards one side (−Z side) in the first direction. The insert body portion 431 is provided with a second housing portion 434. The second housing portion 434 is a hemispherical hole about the center point C, recessed towards the other side (+Z side) in the first direction from the surface on one side in the first direction of the insert body portion 431.

In the insert body portion 431, bearing recesses (recess portions) 433a and 433b are formed on both sides across the central axis AX1 in the second direction X. As shown in FIG. 27, the shaft portions 424a and 424b of the cup 420 are fitted to the bearing recesses 433a and 433b. That is, in the present embodiment, a coupling portion is constituted by the bearing recesses 433a and 433b and the shaft portions 424a and 424b. Due to this, the insert 430 is coupled to the cup 420 so as to be pivotable about the pivotal axis AX2. The protrusion portions 432a and 432b are provided on both sides in the third direction Y of an opening edge portion of the second housing portion 434. The protrusion portions 432a and 432b extend along the circumferential direction. The protrusion height of the protrusion portions 432a and 432b decreases from the circumferential center towards both circumferential sides.

In the present embodiment, the gap between the bearing recesses 433a and 433b and the shaft portions 424a and 424b is sufficiently small. Even in this case, it is possible to obtain the artificial hip joint 410 capable of sufficiently suppressing dislocation while ensuring the range of motion of the joint.

It is to be noted that while in each of the above-described embodiments, the case where the sliding surface between the insert and the cup is a hemispherical or semi-cylindrical surface has been described, the present invention is not limited to this. As long as the insert and the cup are pivotable about the pivotal axis AX2, the sliding surface between the insert and the cup may have any shape.

Further, while in each of the above-described embodiments, the coupling portion is configured to have the recess portion provided in the insert and the projection portion provided in the cup and fitted in the recess portion, the present invention is not limited to this. The configuration of the coupling portion is not particularly limited as long as the insert and the cup are coupled so as to be pivotable about the pivotal axis AX2 and the movement of the insert to one side (−Z side) in the first direction is regulated. For example, the coupling portion may be configured to have a recess portion provided in the cup and a projection portion provided in the insert and fitted to the recess portion. Further, the coupling portion may have a coupling structure other than the recess and projection fitting structure. For example, the coupling portion may have a structure in which the insert and the cup are coupled using screws or the like.

In addition, in the first embodiment, the second embodiment, and the fourth embodiment described above, any one of the protrusion portions may not be provided. Further, the shape of the protrusion portion is not particularly limited.

In addition, while in each of the above-described embodiments, the example of an artificial hip joint is shown as an artificial joint, the invention is not limited to this. The present invention is applicable to any artificial joint other than an artificial hip joint. When applied to other artificial joints, the movable member corresponds to an implant to be embedded in the bone movable with respect to the bone to which the cup is fixed. Each of the above-described configurations can be appropriately combined within a range where they are not inconsistent with each other.

REFERENCE SIGNS LIST 10 artificial hip joint (artificial joint)
12 femoral implant (movable member)
12a bone head portion
12b neck portion
20, 220, 420, 520 cup
24, 421a first housing portion
30, 130, 230, 330, 430 insert
31, 231, 431 insert body portion
32, 32a, 32b, 132a, 132b, 232a, 232b, 432a, 432b protrusion portion
33a, 33b, 233a, 233b, 433a, 433b bearing recess (recess portion)
34, 434 second housing portion
42 shaft body portion (projection portion)
60 coupling portion
224a, 224b, 424a, 424b shaft portion (projection portion)
AX2 pivotal axis
X second direction
Z first direction

What is claimed is:
1. An artificial joint, comprising:
a cup having a first housing portion opening to one side in a first direction;
an insert having a second housing portion opening to one side in the first direction and being housed in the first housing portion;
a movable member having a spherical bone head portion rotatably housed in the second housing portion and a neck portion extending from the bone head portion; and
a coupling portion coupling the insert to the cup so as to be pivotable about a pivotal axis extending in a second direction orthogonal to the first direction and regulates movement to one side in the first direction of the insert relative to the cup, wherein
the neck portion pivots about the pivotal axis and comes into contact with a periphery portion of the insert, thereby pushing a part of the insert into the first housing portion,
the insert pivots about the pivotal axis by the part of the insert being pushed by the neck portion and a portion on a side opposite across the pivotal axis to a side pushed by the neck portion protrudes more to one side in the first direction than the cup,
the coupling portion includes a recess portion provided in one of the cup and the insert, and a projection portion provided in the other of the cup and the insert and fitted in the recess portion,
a top end portion of the projection portion is hemispherical and protrudes to the second direction, and
a gap width of 1 mm to 3 mm in which the insert is movable to an extent that the insert does not completely deviate from the cup is provided between the recess portion and the projection portion.

2. The artificial joint according to claim 1, wherein the insert includes an insert body portion, and a protrusion portion protruding from the insert body portion towards one side in the first direction.

3. The artificial joint according to claim 1, wherein the insert includes an insert body portion, and a protrusion portion protruding from the insert body portion towards one side in the first direction.

4. The artificial joint according to claim 3, wherein the insert includes an insert body portion, and a protrusion portion protruding from the insert body portion towards one side in the first direction.

5. The artificial joint according to claim 4, wherein the protrusion portion is provided on each of both sides across the pivotal axis.

6. The artificial joint according to claim 5, wherein a protrusion height of the protrusion portion decreases from a circumferential center towards both circumferential sides.

7. The artificial joint according to claim 4, wherein a protrusion height of the protrusion portion decreases from a circumferential center towards both circumferential sides.

8. The artificial joint according to claim 3, further comprising a pivot support shaft having a cylindrical shaft body portion, wherein
the projection portion is formed by the shaft body portion,
the cup includes a pivot support shaft insertion hole receiving the pivot support shaft, and
the pivot support shaft is inserted into and fixed to the pivot support shaft insertion hole.

9. The artificial joint according to claim 1, further comprising a pivot support shaft having a cylindrical shaft body portion, wherein
the projection portion is formed by the shaft body portion,
the cup includes a pivot support shaft insertion hole receiving the pivot support shaft, and
the pivot support shaft is inserted into and fixed to the pivot support shaft insertion hole.

10. The artificial joint according to claim 9, wherein the protrusion portion is provided on each of both sides across the pivotal axis.

11. The artificial joint according to claim 10, wherein a protrusion height of the protrusion portion decreases from a circumferential center towards both circumferential sides.

12. The artificial joint according to claim 9, wherein a protrusion height of the protrusion portion decreases from a circumferential center towards both circumferential sides.

13. The artificial joint according to claim 1, wherein the protrusion portion is provided on each of both sides across the pivotal axis.

14. The artificial joint according to claim 13, wherein a protrusion height of the protrusion portion decreases from a circumferential center towards both circumferential sides.

15. The artificial joint according to claim 1, wherein a protrusion height of the protrusion portion decreases from a circumferential center towards both circumferential sides.

* * * * *